United States Patent [19]

Aloup et al.

[11] Patent Number: 5,753,657

[45] Date of Patent: May 19, 1998

[54] IMIDAZO[1,2-A] PYRAZINE-4-ONE, PREPARATION THEREOF AND DRUGS CONTAINING SAME

[75] Inventors: Jean-Claude Aloup, Villeneuve Le Roi; Francois Audiau, Charenton Le Pont; Dominique Damour, Paris; Arielle Genevois-Borella, Thiais; Patrick Jimonet, Villepreux; Serge Mignani, Chatenay-Malabry; Yves Ribeill, Villemoisson Sur Orge, all of France

[73] Assignee: Rhone-Poulenc Rorer S.A., Antony, France

[21] Appl. No.: 583,126

[22] PCT Filed: Jul. 11, 1994

[86] PCT No.: PCT/FR94/00866

§ 371 Date: Jan. 16, 1996

§ 102(e) Date: Jan. 16, 1996

[87] PCT Pub. No.: WO95/02601

PCT Pub. Date: Jan. 26, 1995

[30] Foreign Application Priority Data

Jul. 16, 1993 [FR] France ................. 93 08754

[51] Int. Cl.⁶ ............... A61K 31/495; C07D 241/36
[52] U.S. Cl. ................ 514/250; 544/230; 544/343
[58] Field of Search .............. 544/343, 230; 514/250

[56] References Cited

U.S. PATENT DOCUMENTS 5,196,421  3/1993  McQuaid et al. ............. 514/250

FOREIGN PATENT DOCUMENTS

WO-92/11245  7/1992  WIPO.
WO-94/07893  4/1994  WIPO.

OTHER PUBLICATIONS

CAS Online Structure Search of WO 94/07893, Jan. 10, 1997.

*Primary Examiner*—Mukund J. Shah
*Assistant Examiner*—Brenda Coleman
*Attorney, Agent, or Firm*—Finnegan, Henderson, Farabow, Garrett & Dunner, L.L.P.

[57] ABSTRACT

Compounds of formula (1)

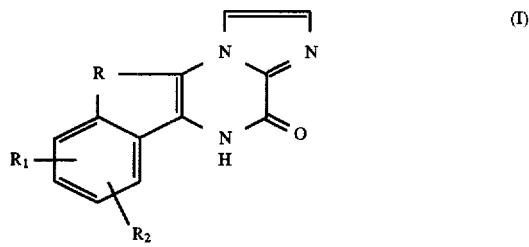

wherein either R is C=$R_3$, C($R_4$)$R_5$ or CH—$R_6$, $R_1$ and $R_2$ are hydrogen, halogen, alkyl, alkoxy, amino, acylamino, —NH—CO—NH—Ar, —N=CH—N(alk)alk', nitro, cyano, phenyl, imidazolyl or $SO_3H$, $R_3$ is oxygen, NOH, NO-alk-COOK or CH—$R_7$, $R_4$ is alkyl, -alk-Het or alk-Ar, $R_5$ is alkyl, -alk-Het or -alk-Ar, or C($R_4$)$R_5$ is cycloalkyl, $R_6$ is hydroxy, alkyl, $NR_8R_9$, -alk-OH, -alk-$NR_8R_9$, -alk-Ar or -alk-Het, $R_7$ is hydroxy, alkyl, phenyl, -alk-Ar, -alk-Het, $NR_{10}R_{11}$ or a heterocyclic ring, $R_8$ and $R_9$ are alkyl, or $R_8$ is hydrogen and $R_9$ is hydrogen or alkyl, —$COR_{12}$, —$CSR_{30}$ or —$SO_2R_{13}$, $R_{10}$ and $R_{11}$ are alkyl or cycloalkyl, $R_{12}$ is alkyl, cycloalkyl, phenyl, —COO-alk, —$CH_2$—COOX, —$CH_2NH_2$, —NH-alk, —NH—Ar, —$NH_2$ or —NH-Het, $R_{13}$ is alkyl or phenyl, $R_{30}$ is —NH-alk, —NH—Ar, —$NH_2$ or —NH-Het, $R_{13}$ is alkyl or phenyl, $R_{30}$ is —NH-alk, —NH—Ar, —$NH_2$ or —NH-Het; or R is a 2-imidazolylmethyl radical and each of $R_1$ and $R_2$ is a hydrogen atom. The compounds of formula (I) are α-amino-3-hydroxy-5-methyl-4-isoxazolepropionic acid (AMPA) receptor antagonists, said receptor also being known as the quisqualate receptor. Furthermore, the compounds of formula (I) are non-competitive N-methyl-D-aspartate (NMDA) receptor antagonists, and especially NMDA receptor gylcine modulation site ligands.

7 Claims, No Drawings

IMIDAZO[1,2-A] PYRAZINE-4-ONE, PREPARATION THEREOF AND DRUGS CONTAINING SAME

This application is a 371 of PCT/FR94/00866 filed Jul. 11, 1994.

The present invention relates to compounds of formula:

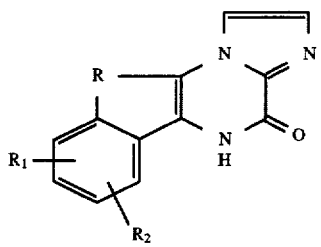

their salts, their preparation and the medicaments containing them.

In the formula (I), either R represents a radical C=$R_3$, C($R_4$)$R_5$ or CH—$R_6$, $R_1$ and $R_2$, which may be identical or different, represent hydrogen or halogen atoms or alkyl, alkoxy, amino, acylamino, —NH—CO—NH—Ar, —N=CH—N(alk)alk', nitro, cyano, phenyl, imidazolyl or $SO_3H$ radicals, $R_3$ represents an oxygen atom or an NOH, NO-alk-COOX or CH—$R_7$ radical, $R_4$ represents an alkyl, -alk-Het or -alk-Ar radical, $R_5$ represents an alkyl (1–11C in a straight or branched chain), -alk-Het or -alk-Ar radical, or alternatively $R_4$ and $R_5$ form, together with the carbon atom to which they are attached, a cycloalkyl radical, $R_6$ represents a hydroxyl, alkyl (1–11C in a straight or branched chain), —$NR_8R_9$, -alk-OH, -alk-$NR_8R_9$, -alk-Ar or -alk-Het radical, $R_7$ represents a hydroxyl, alkyl, phenyl, -alk-Ar, -alk-Het or —$NR_{10}R_{11}$ radical or a saturated or unsaturated mono- or polycyclic heterocyclic radical containing 4 to 9 carbon atoms and one or more hetero atoms (O, S, N), $R_8$ and $R_9$, which may be identical or different, each represent an alkyl radical, or alternatively $R_8$ represents a hydrogen atom and $R_9$ represents a hydrogen atom or an alkyl, —$COR_{12}$, —$CSR_{30}$ or —$SO_2R_{13}$ radical, $R_{10}$ and $R_{11}$, which may be identical or different, each represent an alkyl or cycloalkyl radical, $R_{12}$ represents an alkyl, cycloalkyl, phenyl, —COO-alk, —$CH_2$—COOX, —$CH_2$—$NH_2$, —NH-alk, —$NH_2$, —NH—Ar or —NH-Het radical, $R_{13}$ represents an alkyl or phenyl radical, $R_{30}$ represents an —NH-alk, —NH—Ar, —$NH_2$ or —NH-Het radical, alk represents an alkyl or alkylene radical, alk' represents an alkyl radical, X represents a hydrogen atom or an alkyl radical, Ar represents a phenyl radical and Het represents a saturated or unsaturated mono- or polycyclic heterocycle containing 4 to 9 carbon atoms and one or more hetero atoms (O, S, N);

or R represents a radical CH—$R_6$, $R_6$ represents a 2-imidazolylmethyl radical and $R_1$ and $R_2$ each represent a hydrogen atom.

Except where otherwise mentioned, in the above definitions and those which follow, the alkyl and alkylene radicals and portions contain 1 to 4 carbon atoms in a straight or branched chain, the acyl portions contain 2 to 4 carbon atoms, the cycloalkyl radicals contain 3 to 6 carbon atoms and the halogen atoms are chosen from fluorine, chlorine, bromine and iodine.

The heterocycles mentioned in the above definitions are preferably pyridyl, furyl, quinolyl, pyrazinyl and piperidyl ring systems.

The compounds of formula (I) for which $R_3$ represents a radical NOH, NO-alk-COOX or CH—$R_7$ have isomeric forms (E and Z). These isomers and their mixtures form part of the invention.

The enantiomers and diastereomers of the compounds of formula (I) for which R represents a radical C($R_4$)$R_5$, in which $R_4$ is different from $R_5$ or CH—$R_6$, also form part of the invention.

The compounds of formula (I) for which R represents a radical C=$R_3$, in which $R_3$ represents an oxygen atom, may be prepared by hydrolysis of the corresponding compounds of formula (I) for which R represents a radical C=$R_3$ and $R_3$ represents a radical NOH.

This reaction is generally carried out using an acid, in aqueous medium, at the boiling point of the reaction medium. Hydrochloric acid is preferably used as acid.

The compounds of formula (I) for which R represents a radical C=$R_3$ and $R_3$ represents a radical NOH may be prepared by reacting an alkyl nitrite with a derivative of formula:

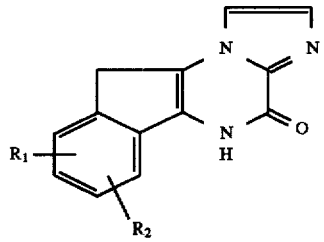

in which $R_1$ and $R_2$ have the same meanings as in the formula (I).

This reaction is preferably carried out in an inert solvent such as dimethyl sulphoxide in the presence of an alkali metal hydride such as sodium hydride, at a temperature in the region of 20° C. Isoamyl nitrite is preferably used.

The derivatives of formula (II) may be prepared by dealkylation and desalification of the derivatives of formula:

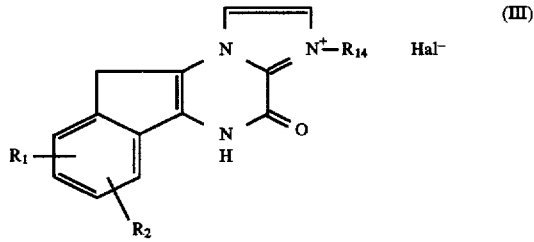

in which $R_1$ and $R_2$ have the same meanings as in the formula (I), $R_{14}$ represents an alkyl radical and Hal represents a halogen atom and preferably a bromine atom.

This reaction is preferably carried out in the presence of imidazole, at a temperature between 100° and 200° C.

The derivatives of formula (III) may be obtained by reacting derivatives of formula:

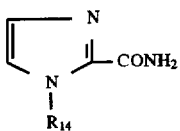

in which $R_{14}$ has the same meanings as in the formula (III), with a 2-haloindanone of formula:

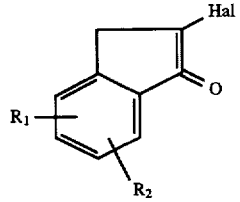

in which $R_1$ and $R_2$ have the same meanings as in the formula (I) and Hal represents a halogen atom.

This reaction is generally carried out in an inert solvent such as dimethylformamide, at a temperature between 50° and 150° C. and preferably at 115° C.

The derivatives of formula (IV) may be obtained by adaptation or application of the method described by D. D. Davey, J. Org. Chem., 52, 4379 (1987).

The 2-haloindanones of formula (V) may be obtained by application or adaptation of the method described by M. Olivier et al., Bull. Soc. Chim. France, 3092 (1973) and in German Patent 2,640,358.

The derivatives of formula (II) may also be obtained by cyclization of a derivative of formula:

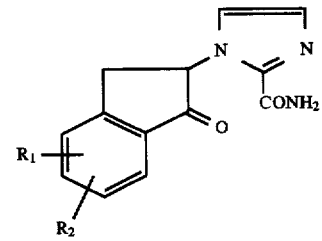

in which $R_1$ and $R_2$ have the same meanings as in the formula (I).

This cyclization is generally performed using an acid such as hydrochloric acid in aqueous solution or acetic acid, at a temperature between 20° C. and the boiling point of the reaction medium.

The derivatives of formula (VI) may be obtained by reacting ammonia with a derivative of formula:

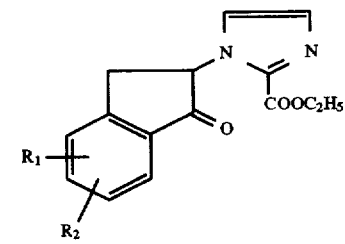

in which $R_1$ and $R_2$ have the same meanings as in the formula (I).

This reaction is generally carried out in an inert solvent such as an alcohol, at a temperature between 20° C. and the boiling point of the reaction medium.

The derivatives of formula (VII) may be obtained by condensing ethyl 2-imidazolecarboxylate with a derivative of formula (V) in which $R_1$ and $R_2$ have the same meanings as in the formula (I) and Hal represents a halogen atom and preferably a bromine atom.

This reaction is carried out either by fusing the reaction medium or in an inert solvent such as an alcohol (methanol or ethanol for example), an aromatic hydrocarbon such as toluene or dimethylformamide, optionally in the presence of a base such as an alkali metal hydride (sodium hydride for example), at a temperature between 20° C. and the boiling point of the reaction medium.

Ethyl 2-imidazolecarboxylate may be obtained according to the method described in U.S. Pat. No. 3,600,399.

The compounds of formula (I) for which R represents a radical C=$R_3$ and $R_3$ represents a radical NO-alk-COOX may be prepared by reacting a corresponding compound of formula (I) for which R represents a radical C—$R_3$ and $R_3$ represents a radical NOH with a halide Hal-alk-COOX for which Hal represents a halogen atom, alk represents an alkyl radical and X represents an alkyl radical, optionally followed by freeing of the carboxyl function by the action of trifluoroacetic acid.

This reaction is preferably carried out in the presence of a base such as an alkali metal hydride, for instance sodium hydride, in an inert solvent such as dimethyl sulphoxide, at a temperature in the region of 20° C. The treatment with trifluoroacetic acid is carried out at a temperature between 5° C. and the boiling point of the reaction medium.

The compounds of formula (I) for which R represents a radical C=$R_3$ and $R_3$ represents a radical CH—$R_7$, in which $R_7$ represents a hydroxyl radical, may be prepared by hydrolysis of the corresponding compounds of formula (I) for which $R_7$ represents a radical —$NR_{10}R_{11}$.

This reaction is preferably carried out using an acid such as hydrochloric acid, in aqueous medium, at a temperature between 20° and 40° C.

The compounds of formula (I) for which R represents a radical C=$R_3$, $R_3$ represents a radical CH—$R_7$ and $R_7$ represents a radical —$NR_{10}R_{11}$ may be prepared by reacting a derivative of formula (II), in which $R_1$ and $R_2$ have the same meanings as in the formula (I), with a derivative of formula:

$$R_{15}$$
$$|$$
$$HC-R_{16}$$
$$|$$
$$R_{17}$$

(VIII)

in which either $R_{15}$ and $R_{17}$, which may be identical or different, each represent a radical —$NR_{10}R_{11}$ and $R_{16}$ represents an alkoxy radical such as tert-butoxy, or $R_{15}$, $R_{16}$ and $R_{17}$ which are identical, each represent a radical —$NR_{10}R_{11}$.

This reaction is generally carried out in an inert solvent such as dimethylformamide, at a temperature between 20° and 40° C.

The derivatives of formula (VIII) may be obtained by application or adaptation of the method described by H. Bredereck, Liebigs Ann. Chem., 762, 62 (1972).

The compounds of formula (I) for which R represents a radical C=$R_3$, $R_3$ represents a radical CH—$R_7$ and $R_7$ represents an alkyl, phenyl, -alk-Het, -alk-Ar or heterocyclic radical may be prepared by reacting a derivative of formula (II), in which $R_1$ and $R_2$ have the same meanings as in the formula (I), with an aldehyde of formula:

$$OHC-R_{18}$$ (IX)

in which $R_{18}$ represents an alkyl, phenyl, -alk-Het, -alk-Ar or Het radical.

This reaction is generally carried out either in an inert solvent such as dimethylformamide, 1,2-dimethoxyethane, an alcohol (methanol or ethanol for example) or a mixture of these solvents, in the presence of a base such as sodium hydroxide, potassium hydroxide, a strong organic base such as 1,8-diazabicyclo[5.4.0]undec-7-ene at a temperature between 20° and 100° C. or in dimethyl sulphoxide, in the presence of an alkali metal hydride such as sodium hydride, at a temperature in the region of 20° C. or in the presence of tetrabutylammonium bromide and a base such as an alkali metal hydroxide (sodium hydroxide or potassium hydroxide for example), in dimethyl sulphoxide, at a temperature between 20° C. and the boiling point of the reaction medium.

The derivatives of formula OHC—$R_{18}$ are commercially available or may be obtained by application or adaptation of the methods described by H. Rutner et al., J. Org. Chem., 28, 1898 (1963). They may also be obtained by (a) oxidation of the corresponding alcohols (using $K_2Cr_2O_7$, in sulphuric medium; using $CrO_3$ in pyridine or using $MnO_2$ in a chlorinated solvent (dichloromethane for example), at a temperature in the region of 20° C. or using dimethyl sulphoxide and ClCO—COCl by adaptation or application of the method described by D. Swern et al., J. Org. Chem., 44, 4148 (1979)); (b) reduction of the corresponding carboxylic acids (using lithium aluminium hydride or $AlH_3$ in an inert solvent such as tetrahydrofuran, at a temperature between 0° and 25° C.); (c) reduction of the corresponding esters (using diisobutylaluminium hydride, in an inert solvent such as toluene, at a temperature between −70° C. and 25° C. or lithium aluminium hydride, in an inert solvent such as tetrahydrofuran, at a temperature between 0° and 25° C.).

The corresponding alcohols HO-alk-Het or HO-alk-Ar are commercially available or may be obtained from the corresponding organometallic compounds by application or adaptation of the methods described by N. S. Narasimhan et al., Tetrahedron Lett., 22 (29)., 2797 (1981); L. Estel et al., J. Het. Chem., 26, 105 (1989); N. S. Narasimhan et al., Synthesis, 957 (1983) and F. Marsais et al., J. Heterocyclic Chem., 25, 81 (1988). Preferably, the organolithium or organomagnesium reagent of the heterocycle or of the benzene is reacted with formaldehyde, an aldehyde, a ketone, an epoxide or Hal-alk-OP, where P is a protecting group (methyl ether, tetrahydropyranyl ether, benzyl ether or triethylsilyl ether for example), followed by freeing the alcohol function, by application or adaptation of the methods described by W. Greene et al., Protecting Groups in Organic Synthesis, second edition, 1991, John Wiley and Sons.

The corresponding alcohols HO-alk-Het or HO-alk-Ar may also be obtained by reducing the corresponding carboxylic acids or esters, using lithium aluminium hydride, in an inert solvent such as tetrahydrofuran or diethyl ether, at the boiling point of the reaction medium.

The alcohols HO-(alk)$_n$-Het may also be obtained by application or adaptation of the method described by J. Th. Meyer et al., Helv. Chem. Acta, 65, 1868 (1982) from derivatives Hal-(alk)$_{n-1}$-Het, which are themselves obtained by reacting a halogenating agent (halogenated phosphorus derivative or thionyl chloride) with a corresponding derivative HO-(alk)$_{n-1}$-Het, optionally in an inert solvent such as dichloromethane, at a temperature between 20° and 40° C.

The corresponding carboxylic acids HOOC-Het, HOOC-alk-Het, HOOC-alk-Ar are commercially available or may be obtained from the corresponding heterocycles and from chlorobenzene, bromobenzene or iodobenzene by application or adaptation of the methods described by L. Estel et al., J. Heterocyclic Chem., 26, 105 (1989); N. S. Narasimhan et al., Synthesis, 957 (1983); A. Turck et al., Synthesis, 881 (1988); A. J. Clarke et al., Tetrahedron Lett., 27, 2373 (1974); A. R. Katritzky et al., Org. Prep. Procedure Int., 20 (6), 585 (1988); N. Furukawa et al., Tetrahedron Lett., 28 (47), 5845 (1987); H. W. Gschwend et al., Organic Reactions, 26, 1 (1979) and V. Snieckus, Chem. Rev., 90, 879 (1990). Preferably, the corresponding organometallic derivative of the heterocycle or of the benzene (organolithium or organomagnesium for example) is prepared, it is reacted either with $CO_2$ or with a derivative Hal-alk-COOalk, in which Hal represents a halogen atom and alk represents an alkyl radical, and the product thus obtained is optionally hydrolysed. This hydrolysis is carried out by any hydrolysis method known to a person skilled in the art and which does not affect the rest of the molecule. The process is preferably performed either using an acid such as hydrochloric acid, in acetic acid at a temperature between 20° and 50° C., or using trifluoroacetic acid, at a temperature between 5° C. and the boiling point of the reaction medium, or in the presence of an alkali metal hydroxide (sodium hydroxide, potassium hydroxide or barium hydroxide for example), in an alcohol such as. methanol or ethanol, at a temperature between 20° C. and the boiling point of the reaction medium. The corresponding esters are commercially available or may be obtained from the acids by the action of an organic acid such as hydrochloric acid or sulphuric acid, in an alcohol which also serves as esterification agent, at the boiling point of the reaction medium. The derivatives Hal-alk-COOalk are commercially available or prepared by reacting Hal-alk-Hal, in which Hal represents a halogen atom and alk an alkyl radical, with an alkali metal cyanide such as sodium or potassium cyanide in a water/alcohol mixture, at a temperature between 0° C. and the boiling point of the reaction medium, followed by the action of an acid such as hydrochloric acid, in the presence of an alcohol, at a temperature between 0° C. and the boiling point of the reaction medium.

The compounds of formula (I) for which R represents a radical $C(R_4)R_5$, $R_4$ represents an alkyl, -alk-Het or -alk-Ar radical and $R_5$ is identical to $R_4$ may be prepared by reacting a derivative of formula (II), in which $R_1$ and $R_2$ have the same meanings as in the formula (I), with a halide of formula:

Hal-$R_{19}$            (X)

in which $R_{19}$ represents an alkyl, -alk-Het or -alk-Ar radical.

This reaction is preferably carried out in an inert solvent such as dimethyl sulphoxide, dimethylformamide, tetrahydrofuran or dioxane, in the presence of a base such as an alkali metal hydroxide (sodium hydroxide or potassium hydroxide for example), optionally in the presence of tetrabutylammonium bromide in dimethyl sulphoxide or in the presence of an alkali metal hydride (sodium hydride for example), at a temperature between 20° C. and the boiling point of the reaction medium.

The halides Hal-$R_{19}$ are commercially available or may be obtained from the corresponding alcohols by application or adaptation of the methods described by R. C. Larock, "Comprehensive Organic Transformations", Ed. VCH, page 353 (1989).

The compounds of formula (I) for which R represents a radical $C(R_4)R_5$, $R_4$ represents an alkyl, -alk-Het or -alk-Ar radical and $R_5$ represents an alkyl (1–11C in a straight or branched chain), -alk-Het or -alk-Ar radical may be prepared by reacting a derivative of formula:

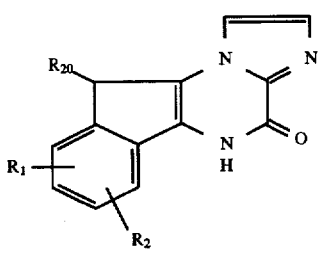
(XI)

in which $R_1$ and $R_2$ have the same meanings as in the formula (I) and $R_{20}$ represents an alkyl, -alk-Het or -alk-Ar radical, or the silyl derivative of this derivative, with a halide of formula:

Hal-$R_{21}$   (XII)

in which $R_{21}$ represents an alkyl (1–11C in a straight or branched chain), -alk-Het or -alk-Ar radical.

This reaction is preferably carried out in an inert solvent such as dimethyl sulphoxide, dimethylformamide, tetrahydrofuran or dioxane, in the presence of a base such as an alkali metal hydroxide (sodium hydroxide or potassium hydroxide for example), optionally in the presence of tetrabutylammonium bromide in dimethyl sulphoxide or in the presence of an alkali metal hydride (sodium hydride for example), at a temperature between 20° C. and the boiling point of the reaction medium. When the silyl derivative is used, it is prepared by reacting trimethylchlorosilane with the derivative of formula (XI), preferably in an inert solvent such as dimethylformamide, in the presence of an alkali metal hydride such as sodium hydride, at a temperature between 5° and 30° C. and the derivative of formula (XII) is reacted in this medium, at a temperature between 5° and 30° C.

The compounds of formula (I) for which R represents a radical $C(R_4)R_5$, $R_4$ represents a radical -alk-Het, in which alk is an ethyl radical and Het is a 4-pyridyl or 2-pyridyl radical, and $R_5$ represents an alkyl (1–11C in a straight or branched chain), -alk-Het or -alk-Ar radical may also be prepared by reacting a derivative of formula (XI), in which $R_1$ and $R_2$ have the same meanings as in the formula (I) and $R_{20}$ represents an alkyl (1–11C in a straight or branched chain), -alk-Het or -alk-Ar radical in its silyl form, with 2- or 4-vinylpyridine.

The silyl derivative is generally obtained by reacting trimethylchlorosilane with the derivative of formula (XI), in an inert solvent such as dimethylformamide, in the presence of an excess (approximately 4 to 5 equivalents) of an alkali metal hydride such as sodium hydride, at a temperature between 5° and 30° C. and the vinyl compound is reacted in this medium at the same temperature.

The compounds of formula (I) for which R represents a radical $C(R_4)R_5$ and $R_4$ and $R_5$ form, together with the carbon atom to which they are attached, a cycloalkyl radical may be prepared by reacting a derivative of formula (II), in which $R_1$ and $R_2$ have the same meanings as in the formula (I), with a derivative of formula:

Hal-alk-Hal   (XIII)

in which Hal represents a halogen atom and alk represents an alkyl radical (2–5C).

This reaction is generally carried out in the presence of tetrabutylammonium bromide and a base such as an alkali metal hydroxide (sodium hydroxide or potassium hydroxide for example) in dimethyl sulphoxide, at a temperature between 20° C. and the boiling point of the reaction medium.

The derivatives of formula (XIII) are commercially available or may be obtained from the corresponding diols by application or adaptation of the methods described by C. Larock, "Comprehensive Organic Transformations", Ed. VCH, page 353 (1989).

The compounds of formula (I) for which R represents a radical CH—$R_6$, in which $R_6$ represents a hydroxyl radical, may be prepared by reducing the corresponding compounds of formula (I), for which R represents a radical C=$R_3$ and $R_3$ represents an oxygen atom.

This reaction is preferably carried out in an inert solvent such as an alcohol (methanol or ethanol for example), in the presence of sodium borohydride, at a temperature between 15° and 40° C.

The compounds of formula (I) for which R represents a 2-imidazolylmethyl or CH—$R_6$ radical, in which $R_6$ represents an alkyl (2–11C), -alk-Ar or -alk-Het radical, may be prepared by hydrogenation of a derivative of formula:

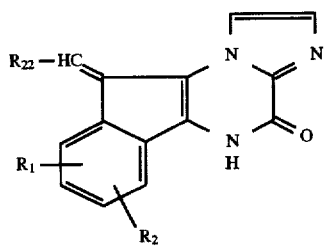
(XIV)

in which $R_1$ and $R_2$ have the same meanings as in the formula (I), $R_{22}$ represents a 2-imidazolyl, alkyl in a straight or branched chain containing 1 to 10 carbon atoms, phenyl, -alk-Ar or -alk-Het radical in which the alkyl portion is in a straight or branched chain and contains 1 to 3 carbon atoms or a saturated or unsaturated mono- or polycyclic heterocyclic radical containing 4 to 9 carbon atoms and one or more hetero atoms (O, S, N).

This reduction is preferably carried out using hydrogen, at a pressure of 1 to 20 bar, in an inert solvent such as dimethylformamide, acetic acid, ethyl acetate, an alcohol (methanol or ethanol for example) or a mixture of these solvents, in the presence of a hydrogenation catalyst such as palladium on charcoal, palladium hydroxide or palladium (N. Rico et al., Nouveau Journal de Chimie, 10, 1, 25 (1986)), at a temperature between 20° C. and 60° C. or by adaptation of the method described by L. M. Strawn et al., J. Med. Chem., 32, 2104 (1989) which consists in reacting the derivative to be reduced with hydroxylamine sulphate and $H_2NOSO_3H$, in aqueous medium, at a pH between 6 and 7, and at a temperature of 10° C.

The derivatives of formula (XIV) for which $R_{22}$ represents an alkyl radical in a straight or branched chain containing 5 to 10 carbon atoms or a 2-imidazolyl radical may be prepared as described above for their lower homologues (compounds of formula (I) for which R represents a radical C=$R_3$, $R_3$ represents a radical —CH—$R_7$ and $R_7$ represents an alkyl radical).

The compounds of formula (I) for which R represents a radical CH—$R_6$, in which $R_6$ represents a methyl radical, may be prepared by reducing the corresponding compounds of formula (I) for which R represents a radical C=$R_3$, $R_3$ represents a radical CH—$R_7$ and $R_7$ represents a hydroxyl or —$NR_{10}R_{11}$ radical.

This reduction is carried out under the conditions described above for the reduction of the compounds of formula (XIV) for which $R_{22}$ represents an alkyl radical.

The compounds of formula (I) for which R represents a radical CH—$R_6$ and $R_6$ represents a radical -alk(1C)—OH may be prepared by reducing the corresponding compounds of formula (I) for which R represents a radical C=$R_3$. $R_3$ represents a radical CH—$R_7$ and $R_7$ represents a hydroxyl radical.

This reduction is generally carried out using a reducing agent such as sodium borohydride, in an inert solvent such as an alcohol (methanol or ethanol for example), at a temperature in the region of 20° C.

The compounds of formula (I) for which R represents a radical CH—$R_6$ and $R_6$ represents a radical -alk(2–4C)—OH may be prepared by reducing the corresponding derivatives of formula (XIV) for which $R_1$ and $R_2$ have the same meanings as in the formula (I) and $R_{22}$ represents a radical -alk(1–3C)—O—$CH_2$—Ar.

This reduction is carried out under the conditions described above for the reduction of the compounds of formula (XIV) for which $R_{22}$ represents an alkyl radical.

The derivatives of formula (XIV) for which $R_1$ and $R_2$ have the same meanings as in the formula (I) and $R_{22}$ represents a radical -alk(1–3C)—O—$CH_2$—Ar may be obtained by reacting a derivative of formula (II) with an aldehyde OHC-alk(1–3C)—O—$CH_2$—Ar.

This reaction is carried out under the same conditions as those mentioned above for the reaction of the derivatives of formula (II) with the aldehydes of formula (IX).

The aldehydes OHC-alk(1–3C)—O—$CH_2$—Ar may be obtained by application or adaptation of the methods described by P. Schorigin et al., Chem. Ber., 68, 838 (1935) and A. Gaiffe et al., C. R. Acad. Sc. Paris, Ser. C, 266, 1379 (1968).

The compounds of formula (I) for which R represents a radical CH—$R_6$ and $R_6$ represents a radical -alk(2–4C)—OH may also be prepared by reacting $(COCl)_2$ with a corresponding derivative of formula (XI) for which $R_1$ and $R_2$ have the same meanings as in the formula (I) and $R_{20}$ represents a radical -alk-COOH, followed by a reduction.

This reaction is carried out in an inert solvent such as dioxane or chloroform. The reduction is preferably carried out using sodium borohydride, in an inert solvent such as dimethylformamide, at a temperature between 10° and 20° C.

The derivatives of formula (XI) for which $R_1$ and $R_2$ have the same meanings as in the formula (I) and $R_{20}$ represents a radical -alk-COOH may be obtained by reducing a derivative of formula (XIV) in which $R_1$ and $R_2$ have the same meanings as in the formula (I) and $R_{22}$ represents a radical -alk(1–3C)—COO-alk or —COO-alk, in which alk represents an alkyl radical, followed by a hydrolysis of the ester thus obtained.

This reduction is carried out under the conditions described above for the reduction of the compounds of formula (XIV) for which $R_{22}$ represents an alkyl radical. The hydrolysis is carried out by any known method and preferably using an acid such as hydrochloric acid, in an inert solvent such as a mixture of dimethyl sulphoxide and an ether (ethyl ether for example), at a temperature between 10° and 30° C.

The derivatives of formula (XIV) in which $R_1$ and $R_2$ have the same meanings as in the formula (I) and $R_{22}$ represents a radical -alk(1–3C)—COO-alk may be obtained in an analogous manner to the preparation of the derivatives of formula (XIV) for which $R_{22}$ represents an alkyl radical, from the derivative OHC-alk(1–3C)—COO-alk.

The derivatives of formula (XIV) in which $R_1$ and $R_2$ have the same meanings as in the formula (I) and $R_{22}$ represents a radical —COO-alk may be obtained by reacting a derivative of formula (II), in which $R_1$ and $R_2$ have the same meanings as in the formula (I), with an alkyl glyoxylate, in an inert solvent such as dimethyl sulphoxide, in the presence of an alkali metal hydride, at a temperature in the region of 20° C.

The compounds of formula (I) for which R represents a radical CH—$R_6$, in which $R_6$ represents a radical —$NR_8R_8$, $R_8$ and $R_9$ each representing a hydrogen atom, may be prepared by hydrolysis of a corresponding compound of formula (I) for which R represents a radical CH—$R_6$, in which $R_6$ represents a radical —$NR_8R_9$, $R_8$ represents a hydrogen atom and $R_9$ represents a radical —$COR_{12}$ and $R_{12}$ represents an alkyl radical.

This hydrolysis is generally carried out using an acid such as hydrochloric acid, in aqueous medium, at the boiling point of the reaction medium.

The compounds of formula (I) for which R represents a radical CH—$R_6$, in which $R_6$ represents a radical —$NR_8R_9$, $R_8$ and $R_9$ each represent a hydrogen atom, may also be prepared by reduction of a corresponding compound of formula (I) for which R represents a radical C—$R_3$ and $R_3$ represents a radical NOH.

This reduction is generally carried out using zinc, in the presence of ammonium acetate and 28% aqueous ammonia, in an alcohol such as ethanol, at the boiling point of the reaction medium.

The compounds of formula (I) for which R represents a radical CH—$R_6$, in which $R_6$ represents a radical —$NR_8R_9$, $R_8$ represents a hydrogen atom and $R_9$ represents a radical —$COR_{12}$ and $R_{12}$ represents an alkyl radical, may be prepared by reacting an acid of formula:

$$R_{24}—COOH \qquad (XV)$$

in which $R_{24}$ represents an alkyl (1–3C) radical with a corresponding compound of formula (I) for which R represents a radical C=$R_3$ and $R_3$ represents a radical NOH, in the presence of a reducing agent.

This reaction is generally carried out at a temperature between 50° and 100° C. Zinc is preferably used as reducing agent.

The compounds of formula (I) for which R represents a radical CH—$R_6$ and $R_6$ represents a radical —$NR_8R_9$ or -alk-$NR_8R_9$ in which $R_8$ and $R_9$, which may be identical or different, each represent an alkyl radical or alternatively $R_8$ represents, a hydrogen atom and $R_9$ represents an alkyl, —$COR_{12}$ or —$SO_2R_{13}$ radical and $R_{12}$ represents an alkyl, cycloalkyl, phenyl, —COO-alk or —$CH_2$—COOX radical, may be prepared by reacting a corresponding compound of formula (I), for which $R_8$ and $R_9$ each represent a hydrogen atom or alternatively $R_8$ represents a hydrogen atom and $R_9$ represents an alkyl radical, with a halide of formula:

$$Hal-R_{27} \qquad (XVI)$$

in which $R_{27}$ represents an alkyl, —$COR_{12}$ or —$SO_2R_{13}$ radical and $R_{12}$ represents an alkyl, cycloalkyl, phenyl, —COO-alk or —$CH_2$—COOX radical and $R_{13}$ has the same meanings as in the formula (I).

This reaction is preferably carried out in an inert solvent such as dimethylformamide, tetrahydrofuran or dimethyl sulphoxide, in the presence of a base such as a tertiary amine (triethylamine for example) or an aromatic base (pyridine for example) or an inorganic base such as an alkali metal hydroxide (sodium hydroxide or potassium hydroxide for example), at a temperature between 20° C. and the boiling point of the reaction medium.

The derivatives Hal-$R_{27}$ are commercially available or those for which $R_{27}$ represents a radical —$COR_{12}$ may be obtained from the corresponding carboxylic acids by application or adaptation of the methods described by B. Helferich et al., Organic Synth. I, 147 and J. Gason, Organic Synth. III, 169 and those for which $R_{27}$ represents a radical —$SO_2R_{13}$ may be obtained by application or adaptation of the methods described in Houben-Weyl, volume 9, pages 390 and 564 (1955).

The compounds of formula (I) for which R represents a radical CH—$R_6$ and $R_6$ represents a radical —$NR_8R_9$ or -alk-$NR_8R_9$, in which $R_8$ represents a hydrogen atom, $R_9$ represents a radical —$COR_{12}$ or —$CSR_{30}$ and $R_{12}$ and $R_{30}$ represent a radical —NH-alk, —$NH_2$, —NH—Ar or —NH-Het, may be prepared by reacting a corresponding compound of formula (I), for which $R_8$ and $R_9$ each represent a hydrogen atom, with a derivative $R_{28}$—N=C=$R_{31}$ for which $R_{28}$ represents a trimethylsilyl, benzoyl, alkyl or phenyl radical or a saturated or unsaturated mono- or polycyclic heterocyclic radical containing 4 to 9 carbon atoms and one or more hetero atoms (O, S, N) and $R_{31}$ represents an oxygen or sulphur atom, optionally followed by a hydrolysis.

This reaction is preferably carried out in an inert solvent such as dimethylformamide, tetrahydrofuran or dioxane, at a temperature between 20° C. and the boiling point of the reaction medium. For the compounds for which $R_{12}$ and $R_{30}$ are radicals $NH_2$, this reaction is followed by a hydrolysis of the silyl derivative or of the benzoyl derivative obtained above, either using water or using an aqueous solution of an inorganic base such as an alkali metal hydroxide (sodium hydroxide or potassium hydroxide for example), at a temperature between 20° C. and the boiling point of the reaction medium.

The derivatives $R_{28}$—N=C=$R_{31}$ are commercially available or may be obtained from the corresponding primary amines by the action of phosgene or thiophosgene by application or adaptation of the methods described by R. L. Shriner et al., Organic Synth., II, 453 and G. M. Dyson, Organic Synth., I, 165; R. J. Slocompie et al., J. Am. Chem. Soc., 72, 1888 (1950) and S. Patai, "The chemistry of cyanates and their thio derivatives", Ed. John Wiley and Sons, pages 619 and 819 (1977). The corresponding primary amines are commercially available or those for which $R_{28}$ represents a radical Het may be obtained by application or adaptation of the methods described by B. A. Tertov et al., Khim. Geterotsikl. Soedin, II, 1552 (1972) and R. C. Larock, "Comprehensive Organic Transformations", Ed. VCH, page 399, which consists in reacting the organolithium or organomagnesium reagent of the heterocycle considered with $PhN_3$, in the presence of acetic acid, of $(PhO)_2PON_3$, of $NH_2OCH_3$ or of $N_3CH_2Si(CH_3)_3$. The organolithium or organomagnesium reagents may be obtained by application or adaptation of the methods described by D. L. Comins et al., J. Org. Chem., 52, 104 (1987); N. Furukawa et al., Tetrahedron Lett., 28 (47), 5845 (1987); A. R. Katritzky et al., Org. Prep. Procedure Int., 20 (6), 585 (1988); A. J. Clarke et al., Tetrahedron Lett., 27, 2373 (1974 and A. W. Gschwen et al., Organic Reactions, 26, 1 (1979).

The compounds of formula (I) for which R represents a radical CH—$R_6$ and $R_6$ represents a radical —$NR_8R_9$ or -alk-$NR_8R_9$, in which $R_8$ represents a hydrogen atom, $R_9$ represents a radical —$COR_{12}$ and $R_{12}$ represents a radical —$CH_2$—$NH_2$, may be prepared by reacting a corresponding compound of formula (I), for which $R_8$ and $R_9$ each represent a hydrogen atom, with an acid HOOC—$CH_2$—NH—$R_{29}$, in which $R_{29}$ represents a protecting group for the amine function such as tert-butoxycarbonyl, followed by a hydrolysis.

This reaction is preferably carried out in an inert solvent such as dimethylformamide, in the presence of hydroxybenzotriazole, 1-(3-dimethylaminopropyl)-3-ethylcarbodiimide and an organic base such as a trialkylamine (triethylamine for example), at a temperature between 0° and 5° C. The hydrolysis is generally carried out using trifluoroacetic acid, at a temperature in the region of 20° C.

The compounds of formula (I) for which R represents a radical CH—$R_6$ in which $R_6$ represents a radical -alk-Ar or -alk-Het may also be prepared by reacting a derivative of formula (II) with a halide of formula:

Hal-$R_{25}$     (XVII)

in which $R_{25}$ represents a radical -alk-Ar or -alk-Het.

This reaction is preferably carried out in an inert solvent such as dimethyl sulphoxide, dimethylformamide, tetrahydrofuran, dioxane or diethyl ether, in the presence of a base such as an alkali metal hydroxide (sodium hydroxide or potassium hydroxide for example), optionally in the presence of tetrabutylammonium bromide or an alkali metal hydride (sodium hydride for example), at a temperature in the region of 20° C.

The compounds of formula (I) for which R represents a radical CH—$R_6$, $R_6$ represents a radical -alk-$NR_8NR_9$, $R_8$ and $R_9$ each representing a hydrogen atom, may be prepared by reacting bromine and sodium hydroxide with a derivative of formula:

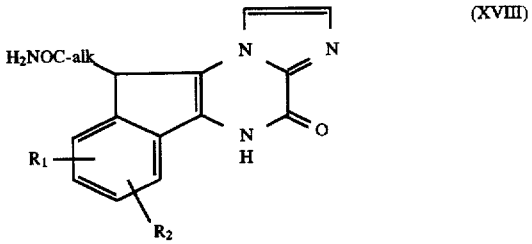

(XVIII)

in which $R_1$ and $R_2$ have the same meanings as in the formula (I) and alk represents an alkyl radical.

This reaction is generally carried out in aqueous medium, at a temperature between 20° and 70° C.

The derivatives of formula (XVIII) may be obtained by reacting ammonia with a derivative of formula:

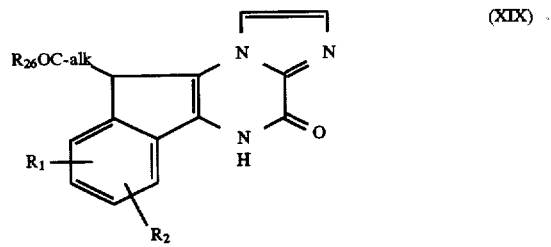

(XIX)

in which $R_1$ and $R_2$ have the same meanings as in the formula (I) and $R_{26}$ represents an alkoxy radical.

This reaction is generally carried out in an inert solvent such as an alcohol, at a temperature in the region of 20° C.

The derivatives of formula (XIX) may be obtained by hydrogenation of the derivatives of formula:

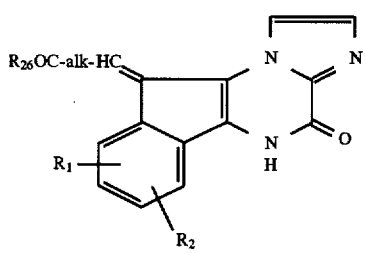

(XX)

in which $R_1$ and $R_2$ have the same meanings as in the formula (I), $R_{26}$ represents an alkoxy radical and alk represents an alkyl (1–3C) radical.

This reduction is carried out under the conditions described above for the reduction of the compounds of formula (XIV) for which $R_{22}$ represents an alkyl radical.

The derivatives of formula (XX) may be obtained by reacting a derivative of formula (II) with an aldehyde of formula:

$$OHC\text{-}alk\text{-}COR_{26} \quad (XXI)$$

in which $R_{26}$ represents an alkoxy radical and alk represents an alkyl (1–3C) radical.

This reaction is generally carried out either in an inert solvent such as dimethylformamide, dimethyl sulphoxide, 1,2-dimethoxyethane, an alcohol (methanol or ethanol for example) or a mixture of these solvents, in the presence of a base such as sodium hydroxide, potassium hydroxide, a strong organic base such as 1,8-diazabicyclo[5.4.0]undec-7-ene, at a temperature between 20° and 100° C., or in dimethyl sulphoxide, in the presence of an alkali metal hydride such as sodium hydride, at a temperature in the region of 20° C., or in the presence of tetrabutylammonium bromide and a base such as an alkali metal-hydroxide (sodium hydroxide or potassium hydroxide for example), in dimethyl sulphoxide, at a temperature between 10° and 100° C.

The derivatives of formula (XXI) are commercially available or may be obtained from the corresponding alcohols by application or adaptation of the methods described by R. C. Larock, "Comprehensive Organic Transformations", Ed. VCH, page 612 (1989). The corresponding alcohols may be obtained by application or adaptation of the method described by H. C. Brown, J. Org. Chem., 31, 485 (1966).

The compounds of formula (I) for which R represents a radical CH—$R_6$, $R_6$ represents a radical —$NR_8R_9$ or -alk-$NR_8R_9$, $R_8$ represents a hydrogen atom and $R_9$ represents an alkyl radical may be prepared by reduction of a corresponding derivative of formula (XI) for which $R_1$ and $R_2$ have the same meanings as in the formula (I) and $R_{20}$ represents a radical —$NR_8R_9$ or -alk-$NR_8R_9$, $R_8$ represents a hydrogen atom and $R_9$ represents a radical —CHO or —$COR_{12}$ in which $R_{12}$ represents an alkyl or cycloalkyl radical.

This reduction is generally carried out in an inert solvent such as tetrahydrofuran, in the presence of $B_2H_6$, at the boiling point of the reaction medium.

The derivatives of formula (XI) for which $R_1$ and $R_2$ have the same meanings as in the formula (I) and $R_{20}$ represents a radical —$NR_8R_9$ or -alk-$NR_8R_9$, $R_8$ represents a hydrogen atom and $R_9$ represents an radical —CHO may be obtained by reacting a corresponding compound of formula (I) for which R represents a radical CH—$R_6$, $R_6$ represents a radical —$NR_8R_9$ or -alk-$NR_8R_9$, $R_8$ represents a hydrogen atom and $R_9$ represents a hydrogen atom with $H_3C$—COOCHO, at a temperature between 0° and 60° C., optionally in the presence of anhydrous sodium acetate.

The compounds of formula (I) for which either R represents a radical $C(R_4)R_5$, in which $R_4$ and/or $R_5$ represents a radical -alk-Het, or R represents a radical CH—$R_6$, $R_6$ represents a radical -alk-Het, in which Het is a piperidyl radical, may also be prepared by hydrogenation of the corresponding compounds of formula (I) for which either R represents a radical $C(R_4)R_5$, in which $R_4$ and/or $R_5$ represents a radical -alk-Het, or R represents a radical CH—$R_6$, $R_6$ represents a radical -alk-Het, in which Het is a pyridyl radical.

This reduction is generally carried out using hydrogen, at a pressure between 1 and 100 bar, in an inert solvent such as dimethylformamide, acetic acid, ethyl acetate, an alcohol (methanol or ethanol for example) or a mixture of these solvents, in the presence of a hydrogenation catalyst such as platinum oxide or Raney nickel, at a temperature between 25° and 100° C.

It is understood by a person skilled in the art that, in order to implement the processes described above according to the invention, it may be necessary to introduce protecting groups for the amino functions for example, in order to avoid side reactions. These groups are those which may be removed without affecting the rest of the molecule. Examples of protecting groups for the amino function which may be mentioned are tert-butyl or methyl carbamates which may be regenerated using iodotrimethylsilane. Other protecting groups which may be used are described by W. Greene et al., Protecting Groups in Organic Synthesis, second edition, 1991, John Wiley & Sons.

The compounds of formula (I) may be purified by the usual known methods, for example by crystallization, chromatography or extraction.

The enantiomers of the compounds of formula (I) for which R represents a radical $C(R_4)$ $R_5$, in which $R_4$ is different from $R_5$ or CH—$R_6$, may be obtained by resolution of the racemic mixtures, for example by chromatography on a chiral column according to W. H. Pirckle et al., asymmetric synthesis, vol. 1, Academic Press (1983) or by synthesis from chiral precursors.

The diastereomers of the compounds of formula (I) for which R represents a radical $C(R_4)R_5$, in which $R_4$ is different from $R_5$ or CH—$R_6$, containing one or more chiral carbons and the various E and Z isomers of the compounds of formula (I) may be separated by the usual known methods, for example by crystallization or chromatography.

The compounds of formula (I) which contain a basic residue may optionally be converted to addition salts with an inorganic or organic acid by the action of such an acid in an organic solvent such as an alcohol, a ketone, an ether or a chlorinated solvent.

The compounds of formula (I) which contain an acid residue may optionally be converted to metal salts or to addition salts with nitrogen-containing bases according to methods known per se. These salts may be obtained by reacting a metallic base (alkali metal or alkaline-earth metal for example), ammonia, an amine or an amine salt with a compound of formula (I), in a solvent. The salt formed is separated by the usual methods.

These salts also form part of the invention.

As examples of pharmaceutically acceptable salts there may be mentioned the addition salts with inorganic or organic acids (such as acetate, propionate, succinate, benzoate, fumarate, maleate, oxalate, methanesulphonate, isethionate, theophyllineacetate, salicylate, methylenebis-β-oxynaphthoate, hydrochloride, sulphate, nitrate and phosphate), salts with alkali metals (sodium, potassium and lithium) or with alkaline-earth metals (calcium and magnesium), the ammonium salt, salts of nitrogen-containing bases (ethanolamine, trimethylamine, methylamine, benzylamine, N-benzyl-β-phenethylamine, choline, arginine, leucine, lysine and N-methylglucamine).

The compounds of formula (I) have advantageous pharmacological properties. These compounds are antagonists of the α-amino-3-hydroxy-5-methyl-4-isoxazolepropionic acid (AMPA) receptor, also known as the quisqualate receptor.

Moreover, the compounds of formula (I) are non-competitive antagonists of the N-methyl-D-aspartate (NMDA) receptor and, more particularly, they are ligands for the glycine regulatory sites of the NMDA receptor.

These compounds are thus useful for treating or preventing all ischemias (such as focal or global ischemia) following cerebrovascular accidents, cardiac arrest, arterial hypotension, cardiac or pulmonary surgical intervention or severe hypoglycaemia. They are also useful in the treatment of effects due to anoxia, whether it be perinatal or following either a drowning or cerebrospinal lesions. These compounds may also be used for treating or preventing the development of neurodegenerative diseases, Huntington's chorea, Alzheimer's disease, amyotrophic lateral sclerosis, olivopontocerebellar atrophy and Parkinson's disease. These compounds may also be used with regard to epileptogenic and/or convulsive symptoms, for the treatment of cerebral or spinal trauma, trauma associated with degeneration of the inner ear (R. Pujol et al., Neuroreport, 3, 299–302 (1992)) or of the retina (J. L. Monsinger et al., Exp. Neurol., 113, 10–17 (1991)), of anxiety (Kehne et al., Eur. J. Pharmacol., 193, 283 (1991)), depression (Trullas et al., Eur. J. Pharmacol., 185, 1 (1990)), schizophrenia (Reynolds, TIPS, 13, 116 (1992)), Tourette's syndrome, hepatic encephalopathies, as analgesics (Dickenson et al., Neurosc. Letters, 121, 263 (1991)), as anti-inflammatory agents (Sluta et al., Neurosci. Letters, 149, 99–102 (1993)), as anti-anorexic agents (Sorrels et al., Brain Res., 572, 265 (1992)), as anti-migraine and anti-emetic agents and for the treatment of poisoning by neurotoxins or other substances which are agonists of the NMDA receptor, as well as neurological problems associated with viral diseases such as AIDS (Lipton et al., Neuron, 7, 111 (1991)), rabies, measles and tetanus (Bagetta et al., Br. J. Pharmacol., 101, 776 (1990)). These compounds are also useful for the prevention of the withdrawal symptoms to drugs and alcohol, and for inhibiting the addiction to and dependency on opiates. They may also be used in the treatment of deficiencies associated with mitochondrial anomalies such as mitochondrial myopathy, Leber's syndrome, Wernicke's encephalopathy, Rett's syndrome, homocysteinaemia, hyperprolinaemia, hydroxybutyric aminoaciduria, Lead's encephalopathy and sulphite oxidase deficiency.

The affinity of the compounds of formula (I) for the AMPA receptor was determined by studying the antagonism of the specific binding of [$^3$H]-AMPA to rat cerebral cortex membranes (Honore et al., Neuroscience Letters, 54, 27 (1985)). The [$^3$H]-AMPA is incubated in the presence of 0.2 mg of proteins at 4° C. for 30 minutes in 10 mM $KH_2PO_4$ buffer, 100 mM KSCN, pH 7.5. The non-specific binding is determined in the presence of 1 mM L-glutamate. The bound radioactivity is separated by filtration through Pharmacia filters (Printed Filtermate A). The inhibitory activity of these products is less than or equal to 100 µM.

The affinity of the compounds of formula (I) for the glycine site bound to the NMDS receptor was determined by studying the antagonism of the specific binding of [$^3$H]-DCKA to rat cerebral cortex membranes according to the method described by T. Canton et al., J. Pharm. Pharmacol., 44, 812 (1992). The [$^3$H]-DCKA (20 nm) is incubated in the presence of 0.1 mg of proteins at 4° C. for 30 minutes in 50 mM HEPES buffer, pH 7.5. The non-specific binding is determined in the presence of 1 mM glycine. The bound radioactivity is separated by filtration through Whatman GF/B filters. The inhibitory activity of these products is less than or equal to 100 µM.

The compounds of formula (I) are of low toxicity. Their $LD_{50}$ is greater than 50 mg/kg via the i.p. route in mice.

Of particular advantage are the compounds of formula (I) for which either R represents a radical C=$R_3$, $C(R_4)R_5$ or CH—$R_6$. $R_1$ and $R_2$ represent hydrogen or halogen atoms, $R_3$ represents an oxygen atom or a radical NO-alk-COOX or CH—$R_7$, $R_4$ represents an alkyl or -alk-Ar radical, $R_5$ represents an alkyl (1–11C in a straight or branched chain), -alk-Het or -alk-Ar radical or alternatively $R_4$ and $R_5$ form, together with the carbon atom to which they are attached, a cycloalkyl radical, $R_6$ represents a hydroxyl, alkyl (1–11C in a straight or branched chain), —$NR_8R_9$, -alk-$NR_8R_9$, -alk-OH, -alk-Ar or -alk-Het radical, $R_7$ represents a hydroxyl, —$NR_{10}R_{11}$ or a saturated or unsaturated mono- or polycyclic heterocyclic radical containing 4 to 9 carbon atoms and one or more hetero atoms (O, S, N), $R_8$ represents a hydrogen atom and $R_9$ represents a hydrogen atom or an alkyl, —$COR_{12}$ or —$SO_2R_{13}$ radical, $R_{10}$ and $R_{11}$, which may be identical or different, each represent an alkyl radical, $R_{12}$ represents an alkyl, —NH—Ar, —NH-alk or phenyl radical, $R_{13}$ represents an alkyl or phenyl radical, alk represents an alkyl or alkylene radical, X represents an alkyl radical, and Het represents a saturated or unsaturated mono- or polycyclic heterocycle containing 4 to 9 carbon atoms and one or more hetero atoms (O, S, N) or alternatively R represents a 2-imidazolylmethyl radical and $R_1$ and $R_2$ are hydrogen atoms.

The following compounds are of particular interest:

10-hydroxy-5H,10H-imidazo[1,2-a]indeno[1,2-e]-pyrazin-4-one, 10-acetamido-5H,10H-imidazo[1,2-a]indeno[1,2-e]-pyrazin-4-one, 10-amino-5H,10H-imidazo[1,2-a]indeno[1,2-e]-pyrazin-4-one, 10-(E-dimethylaminomethylene)-5H,10H-imidazo-[1,2-a]indeno[1,2-e]pyrazin-4-one, 10-hydroxymethylene-5H,10H-imidazo[1,2-a]indeno-[1,2-e]pyrazin-4-one, 10,10-dimethyl-5H,10H-imidazo[1,2-a]indeno[1,2-e]-pyrazin-4-one, spiro[5H,10H-imidazo[1,2-a]indeno[1,2-e]pyrazine-10:1'-cyclopropane]-4-one, spiro[5H,10H-imidazo[1,2-a]indeno[1,2-e]pyrazine-10:1'-cyclopentane]-4-one, 10-methyl-5H,10H-imidazo[1,2-a]indeno[1,2-e]-pyrazin-4-one, 10,10-dibenzyl-5H,10H-imidazo[1,2-a]indeno[1,2-e]-pyrazin-4-one, 10-hydroxymethyl-5H,$_{10}$H-imidazo[1,2-a]indeno-[1,2-e]pyrazin-4-one, 10-(2-furylmethyl)-5H,10H-imidazo[1,2-a]indeno-[1,2-e]pyrazin-4-one, 10-(4-pyridylmethylene)-5H,10H-imidazo[1,2-a]-indeno[1,2-e]pyrazin-4-one, 10-(4-pyridylmethyl)-5H,10H-imidazo[1,2-a]indeno-[1,2-e]pyrazin-4-one, 10-(phenylpropyl)-5H,10H-imidazo[1,2-a]indeno-[1,2-e]pyrazin-4-one, 10-(3-pyridylmethylene)-5H,10H-imidazo[1,2-a]-indeno[1,2-e]pyrazin-4-one, 10-(3-pyridylmethyl)-5H,10H-imidazo[1,2-a]indeno-[1,2-e]pyrazin-4-one, 10-(2-pyridylmethyl)-5H,10H-imidazo[1,2-a]indeno-[1,2-e]pyrazin-4-one, 10-(2-imidazolylmethyl)-5H,10H-imidazo[1,2-a]-indeno[1,2-e]pyrazin-4-one, tert-butyl(4-oxo-5H,10H-imidazo[1,2-a]indeno-[1,2-e]pyrazin-10-ylidene)aminooxyacetate 10-isobutyl-5H,10H-imidazo[1,2-a]indeno[1,2-e]-pyrazin-4-one, (4-oxo-5H,10H-imidazo[1,2-a]indeno[1,2-e]pyrazine-10-ylidene)aminooxyacetic acid, 10-propionamido-5H,10H-imidazo[1,2-a]indeno-[1,2-e]pyrazin-4-one, 10-amino-8-fluoro-5H,10H-imidazo[1,2-a]indeno-[1,2-e]pyrazin-4-one, 10-(4-quinolylmethylene)-5H,10H-imidazo[1,2-a]-indeno[1,2-e]pyrazin-4-one, 10-(4-quinolinylmethyl)-5H,10H-imidazo[1,2-a]-indeno[1,2-e]pyrazin-4-one, 10-(3-phenylureido)-5H,10H-imidazo[1,2-a]indeno-[1,2-e]pyrazin-4-one, 10-(3-methylureido)-5H,10H-imidazo[1,2-a]indeno-[1,2-e]pyrazin-4-one, 10-isobutyramido-5H,10H-imidazo[1,2-a]indeno-[1,2-e]pyrazin-4-one, 10-amino-7-chloro-5H,10H-imidazo[1,2-a]indeno-[1,2-e]pyrazin-4-one, 10-benzenesulphonylamido-5H,10H-imidazo[1,2-a]-indeno[1,2-e]pyrazin-4-one, 10-methylamino-5H,10H-imidazo[1,2-a]indeno[1,2-e]-pyrazin-4-one, 10-(2-pyrazinylmethylene)-5H,10H-imidazo[1,2-a]-indeno[1,2-e]pyrazin-4-one, 10-(2-pyrazinylmethyl)-5H,10H-imidazo[1,2-a]-indeno[1,2-e]pyrazin-4-one, 10-benzyl-7-chloro-5H,10H-imidazo[1,2-a]indeno-[1,2-e]pyrazin-4-one, 7-chloro-10-(3-phenylureido)-5H,10H-imidazo-[1,2-a]indeno[1,2-e]pyrazin-4-one, 10-(2-hydroxyethyl)-5H,10H-imidazo[1,2-a]indeno-[1,2-e]pyrazin-4-one, 7-chloro-10-methylamino-5H,10H-imidazo[1,2-a]-indeno[1,2-e]pyrazin-4-one, 10-benzyl-10-methyl-5H,10H-imidazo[1,2-a]indeno-[1,2-e]pyrazin-4-one, 10-methyl-10-(4-pyridylmethyl)-5H,10H-imidazo-[1,2-a]indeno[1,2-e]pyrazin-4-one, 10-(4-piperidylmethyl)-5H,10H-imidazo[1,2-a]-indeno[1,2-e]pyrazin-4-one, 5H,10H-imidazo[1,2-a]indeno[1,2-e]pyrazine-4,10-dione, 10-benzyl-5H,10H-imidazo[1,2-a]indeno[1,2-e]-pyrazin-4-one, 10-hexyl-5H,10H-imidazo[1,2-a]indeno[1,2-e]-pyrazin-4-one, 10-benzamido-5H,10H-imidazo[1,2-a]indeno[1,2-e]-pyrazin-4-one, 10-methyl-10-[2-(4-pyridyl)ethyl]-5H,10H-imidazo-[1,2-a]indeno[1,2-e]pyrazin-4-one.

The following compounds are particularly interesting with respect to the AMPA receptor:

10-hydroxy-5H,10H-imidazo[1,2-a]indeno[1,2-e]-pyrazin-4-one, 10-acetamido-5H,10H-imidazo[1,2-a]indeno[1,2-e]-pyrazin-4-one, 10-amino-5H,10H-imidazo[1,2-a]indeno[1,2-e]-pyrazin-4-one, 10-(E-dimethylaminomethylene)-5H,10H-imidazo-[1,2-a]indeno[1,2-e]pyrazin-4-one, 10-hydroxymethylene-5H,10H-imidazo[1,2-a]indeno-[1,2-e]pyrazin-4-one, 10,10-dimethyl-5H,10H-imidazo[1,2-a]indeno[1,2-e]-pyrazin-4-one, spiro[5H,10H-imidazo[1,2-a]indeno[1,2-e]pyrazine-10:1'-cyclopropane]-4-one, spiro[5H,10H-imidazo[1,2-a]indeno[1,2-e]pyrazine-10:1'-cyclopentane]-4-one, 10-methyl-5H,10H-imidazo[1,2-a]indeno[1,2-e]-pyrazin-4-one, 10-hydroxymethyl-5H,10H-imidazo[1,2-a]indeno-[1,2-e]pyrazin-4-one, 10-(2-furylmethyl-5H,$_{10}$H-imidazo[1,2-a]indeno-[1,2-e]pyrazin-4-one, 10-(4-pyridylmethylene)-5H,10H-imidazo[1,2-a]-indeno[1,2-e]pyrazin-4-one, 10-(4-pyridylmethyl)-5H,10H-imidazo[1,2-a]indeno-[1,2-e]pyrazin-4-one, 10-(phenylpropyl)-5H,10H-imidazo[1,2-a]indeno-[1,2-e]pyrazin-4-one, 10-(3-pyridylmethylene)-5H,10H-imidazo[1,2-a]-indeno[1,2-e]pyrazin-4-one, 10-(3-pyridylmethyl)-5H,10H-imidazo[1,2-a]indeno-[1,2-e]pyrazin-4-one, 10-(2-pyridylmethyl)-5H,10H-imidazo[1,2-a]indeno-[1,2-e]pyrazin-4-one, 10-(2-imidazolylmethyl)-5H,10H-imidazo[1,2-a]-indeno[1,2-e]pyrazin-4-one, 10-isobutyl-5H,10H-imidazo[1,2-a]indeno[1,2-e]-pyrazin-4-one, (4-oxo-5H,10H-imidazo[1,2-a]indeno[1,2-e]pyrazin-10-ylidene)aminooxyacetic acid, 10-propionamido-5H,10H-imidazo[1,2-a]indeno-[1,2-e]pyrazin-4-one, 10-amino-8-fluoro-5H,10H-imidazo[1,2-a]indeno-[1,2-e]pyrazin-4-one, 10-(3-methylureido)-5H,10H-imidazo[1,2-a]indeno-[1,2-e]pyrazin-4-one, 10-isobutyramido-5H,10H-imidazo[1,2-a]indeno-[1,2-e]pyrazin-4-one, 10-amino-7-chloro-5H,10H-imidazo[1,2-a]indeno-[1,2-e]pyrazin-4-one, 10-benzenesulphonylamido-5H,10H-imidazo[1,2-a]-indeno[1,2-e]pyrazin-4-one, 10-methylamino-5H,10H-imidazo[1,2-a]indeno[1,2-e]-pyrazin-4-one, 10-(2-pyrazinylmethylene)-5H,10H-imidazo[1,2-a]-indeno[1,2-e]pyrazin-4-one, 10-(2-pyrazinylmethyl)-5H,10H-imidazo[1,2-a]-indeno[1,2-e]pyrazin-4-one, 10-(2-hydroxyethyl)-5H,10H-imidazo[1,2-a]indeno-[1,2-e]pyrazin-4-one, 7-chloro-10-methylamino-5H,10H-imidazo[1,2-a]-indeno[1,2-e]pyrazin-4-one.

10-methyl-10-(4-pyridylmethyl)-5H,10H-imidazo-[1,2-a]indeno[1,2-e]pyrazin-4-one.

10-(4-piperidylmethyl)-5H,10H-imidazo[1,2-a]-indeno[1,2-e]pyrazin-4-one.

10-benzyl-7-chloro-5H,10H-imidazo[1,2-a]indeno-[1,2-e]pyrazin-4-one.

5H,10H-imidazo[1,2-a]indeno[1,2-e]pyrazine-4,10-dione.

10-(3-phenylureido)-5H,10H-imidazo[1,2-a]indeno-[1,2-e]pyrazin-4-one.

7-chloro-10-(3-phenylureido)-5H,10H-imidazo-[1,2-a]indeno[1,2-e]pyrazin-4-one.

10-methyl-10-[2-(pyrid-4-yl)ethyl]-5H,10H-imidazo-[1,2-a]indeno[1,2-e]pyrazin-4-one.

The following compounds are particularly interesting with respect to the glycine regulatory site:

10-hydroxy-5H,10H-imidazo[1,2-a]indeno[1,2-e]-pyrazin-4-one.

10-acetamido-5H,10H-imidazo[1,2-a]indeno[1,2-e]-pyrazin-4-one.

10-amino-5H,10H-imidazo[1,2-a]indeno[1,2-e]-pyrazin-4-one.

10-(E-dimethylaminomethylene)-5H,10H-imidazo-[1,2-a]indeno[1,2-e]pyrazin-4-one.

10-hydroxymethylene-5H,10H-imidazo[1,2-a]indeno-[1,2-e]pyrazin-4-one.

10,10-dimethyl-5H,10H-imidazo[1,2-a]indeno[1,2-e]-pyrazin-4-one.

spiro[5H,10H-imidazo[1,2-a]indeno[1,2-e]pyrazine-10:1'-cyclopropane]-4-one.

spiro[5H,10H-imidazo[1,2-a]indeno[1,2-e]pyrazine-10:1'-cyclopentane]-4-one.

10-methyl-5H,10H-imidazo[1,2-a]indeno[1,2-e]-pyrazin-4-one.

10,10-dibenzyl-5H,10H-imidazo[1,2-a]indeno[1,2-e]-pyrazin-4-one.

10-hydroxymethyl-5H,10H-imidazo[1,2-a]indeno-[1,2-e]pyrazin-4-one.

10-(2-furylmethyl)-5H,10H-imidazo[1,2-a]indeno-[1,2-e]pyrazin-4-one.

10-(4-pyridylmethyl)-5H,10H-imidazo[1,2-a]indeno-[1,2-e]pyrazin-4-one.

10-(phenylpropyl)-5H,10H-imidazo[1,2-a]indeno-[1,2-e]pyrazin-4-one.

10-(3-pyridylmethyl)-5H,10H-imidazo[1,2-a]indeno-[1,2-e]pyrazin-4-one.

10-(2-pyridylmethyl)-5H,10H-imidazo[1,2-a]indeno-[1,2-e]pyrazin-4-one.

10-(2-imidazolylmethyl)-5H,10H-imidazo[1,2-a]-indeno[1,2-e]pyrazin-4-one.

10-isobutyl-5H,10H-imidazo[1,2-a]indeno[1,2-e]-pyrazin-4-one.

(4-oxo-5H,10H-imidazo[1,2-a]indeno[1,2-e]pyrazine-10-ylidene)aminooxyacetic acid.

10-propionamido-5H,10H-imidazo[1,2-a]indeno-[1,2-e]pyrazin-4-one.

10-(4-quinolylmethylene)-5H,10H-imidazo[1,2-a]-indeno[1,2-e]pyrazin-4-one.

10-(4-quinolylmethyl)-5H,10H-imidazo[1,2-a]indeno-[1,2-e]pyrazin-4-one.

10-(3-phenylureido)-5H,10H-imidazo[1,2-a]indeno-[1,2-e]pyrazin-4-one.

10-(3-methylureido)-5H,10H-imidazo[1,2-a]indeno-[1,2-e]pyrazin-4-one.

10-isobutyramido-5H,10H-imidazo[1,2-a]indeno-[1,2-e]pyrazin-4-one.

10-amino-7-chloro-5H,10H-imidazo[1,2-a]indeno-[1,2-e]pyrazin-4-one.

10-benzenesulphonylamido-5H,10H-imidazo[1,2-a]-indeno[1,2-e]pyrazin-4-one.

10-methylamino-5H,10H-imidazo[1,2-a]indeno[1,2-e]-pyrazin-4-one.

10-(2-pyrazinylmethyl)-5H,10H-imidazo[1,2-a]-indeno[1,2-e]pyrazin-4-one.

10-benzyl-7-chloro-5H,10H-imidazo[1,2-a]indeno-[1,2-e]pyrazin-4-one.

7-chloro-10-(3-phenylureido)-5H,10H-imidazo-[1,2-a]indeno[1,2-e]pyrazin-4-one.

7-chloro-10-methylamino-5H,10H-imidazo[1,2-a]-indeno[1,2-e]pyrazin-4-one.

10-benzyl-10-methyl-5H,10H-imidazo[1,2-a]indeno-[1,2-e]pyrazin-4-one.

10-methyl-10-(4-pyridylmethyl)-5H,10H-imidazo-[1,2-a]indeno[1,2-e]pyrazin-4-one.

10-benzyl-5H,10H-imidazo[1,2-a]indeno[1,2-e]-pyrazin-4-one.

10-hexyl-5H,10H-imidazo[1,2-a]indeno[1,2-e]-pyrazin-4-one.

10-benzamido-5H,10H-imidazo[1,2-a]indeno[1,2-e]-pyrazin-4-one.

10-(2-hydroxyethyl)-5H,10H-imidazo[1,2-a]indeno-[1,2-e]pyrazin-4-one.

10-methyl-10-[2-(4-pyridyl)ethyl]-5H,10H-imidazo-[1,2-a]indeno[1,2-e]pyrazin-4-one.

The examples which follow illustrate the invention.

EXAMPLE 1

0.4 g of 80% sodium hydride is added to a suspension of 1.1 g of 5H,10H-imidazo[1,2-a]indeno-[1,2-e]pyrazin-4-one in 10 ml of anhydrous dimethyl sulphoxide. After stirring for 10 minutes at a temperature in the region of 20° C., a solution of 0.7 g of isoamyl nitrite in 2 ml of anhydrous dimethyl sulphoxide is added dropwise over 5 minutes and the mixture is then stirred for 1 hour at the same temperature. 10 ml of distilled water are added slowly and the mixture is subsequently poured into 120 g of water and ice, acidified with 1 ml of acetic acid and then centrifuged. After removal of the supernatant solution, the solid is suspended in 25 ml of distilled water, filtered, washed with 10 ml of acetone and dried under reduced pressure (15 mmHg; 2 kPa) at 20° C. The product obtained (1.5 g) is dissolved in 100 ml of boiling dimethylformamide and, after 0.1 g of decolorizing charcoal has been added, the solution is filtered while hot, cooled, poured into 800 ml of distilled water and centrifuged. The solid is suspended in 20 ml of distilled water, filtered, washed with 20 ml of acetone and dried under reduced pressure (15 mmHg; 2 kPa) at 20° C. The product obtained (0.9 g) is dissolved in 75 ml of dimethyl sulphoxide at 20° C. and, after 0.1 g of decolorizing charcoal has been added, the solution is filtered. The filter is washed twice with 20 ml in total of dimethyl sulphoxide and the filtrate and the washings are then combined, 75 ml of distilled water are added and they are centrifuged. The solid is suspended in 25 ml of distilled water, filtered, washed twice with 50 ml in total of acetone and then dried under reduced pressure (1 mmHg; 0.13 kPa) at 60° C. 0.63 g of 10-(E-hydroxyimino)-5H,10H-imidazo[1,2-a]indeno[1,2-e]pyrazin-4-one is thus obtained, decomposing without melting above 300° C. [N.M.R. spectrum: (200 MHz; DMSO $d_6$; δ in ppm): 7.40 and 7.48 (2t, J=7 Hz, 2H: —H7 and —H8); 7.60 and 8.00 (2s broad, 1H each: —H of the imidazole); 7.82 and 8.20 (2d, J=7 Hz, 1H each: —H6 and —H9); 12.70 and 13.00 (2 cplx, 1H each: —NH— and —OH)].

5H,10H-Imidazo[1,2-a]indeno[1,2-e]pyrazin-4-one may be prepared in the following way: a solution of 4.8 g of 3-methyl-4-oxo-5H,10H-imidazo[1,2-a]indeno-[1,2-e]pyrazinium bromide in 30 g of imidazole is heated for 24 hours at 160° C., cooled to 100° C. and then poured into a stirred mixture of 75 g of ice and 75 g of distilled water. The insoluble material is filtered off, washed twice with 20 ml in total of distilled water and then dried under reduced pressure (10 mmHg; 1.3 kPa) at 50° C. The product thus obtained (4 g) is dissolved in 80 ml of dimethylformamide and, after the addition of 20 g of silica, the solution is concentrated to dryness under reduced pressure (15 mmHg; 2 kPa) at 100° C. The mixture is introduced into a column of diameter 4.2 cm containing 240 g of silica and is then eluted with a dichloromethane/methanol mixture (97/3 by volume), collecting 60 ml fractions. Fractions 10 to 70 are combined and, after the addition of 1.5 g of decolorizing charcoal, they are filtered and concentrated to dryness under reduced pressure (15 mmHg; 2 kPa) at 55° C. The product obtained (1.7 g) is dissolved in 350 ml of boiling methanol and, after the addition of 0.1 g of decolorizing charcoal, the solution is filtered while hot and concentrated under reduced pressure (15 mmHg; 2 kPa) at 40° C. in order to bring its volume to approximately 30 ml, and is then stored at 5° C. for 60 hours. The crystals are separated out by filtration, washed twice with 20 ml in total of chilled methanol and dried under reduced pressure (1 mmHg; 0.13 kPa) at 60° C. 1.1 g of 5H,10H-imidazo[1,2-a]indeno[1,2-e]pyrazin-4-one are thus obtained, decomposing without melting at 350° C. [Rf=0.77, thin layer chromatography on silica gel, solvent: dichloromethane/methanol (8/2 by volume)].

3-Methyl-4-oxo-5H,10H-imidazo[1,2-a]indeno-[1,2-e]pyrazinium bromide may be prepared in the following way: a solution of 5 g of 1-methyl-1H-imidazole-2-carboxamide and 12 g of 85% 2-bromoindanone in 100 ml of anhydrous dimethylformamide is stirred for 28 hours at 115° C. and is then cooled to a temperature in the region of 20° C. The insoluble material is separated out by filtration, washed twice with 20 ml in total of chilled dimethylformamide and dried under reduced pressure (10 mmHg; 1.3 kPa). 4.8 g of 3-methyl-4-oxo-5H,10H-imidazo[1,2-a]indeno[1,2-e]pyrazinium bromide are thus obtained [N.M.R. spectrum: (200 MHz; DMSO $d_6$; δ in ppm): 4.13 (s, 2H —$CH_2$ at 10); 4.34 (s, 3H: $N^+$ —$CH_3$); 7.47 (mt, 2H: —H7 and —H8); 7.68 and 7.96 (2d, J=7.5 Hz, 1H each: —H6 and —H9); 8.32 and 8.45 (2d, J=1 Hz, 1H each: H of the imidazole); 13.60 (cplx, 1H: NH)].

1-Methyl-1H-imidazole-2-carboxamide may be prepared according to the process described by D. D. Davey, J. Org. Chem., 52, 4379 (1987).

EXAMPLE 2

A suspension of 1.5 g of 10-(hydroxyimino)-5H,10H-imidazo[1,2-a]indeno[1,2-e]pyrazin-4-one in 90 ml of approximately 5N aqueous hydrochloric acid solution is stirred while boiling for 7 hours, cooled and then concentrated to dryness under reduced pressure (15 mmHg; 2 kPa) at 70° C. The product obtained (2 g) is dissolved in 50 ml of dimethylformamide and, after addition of 0.1 g of decolorizing charcoal, the solution is filtered and the filter is then washed 3 times with 30 ml in total of dimethylformamide. The filtrate and the washings are combined, 600 ml of distilled water are added and they are centrifuged. The solid is suspended in 20 ml of distilled water, filtered, washed with 20 ml in total of acetone and dried under reduced pressure (1 mmHg; 0.13 kPa) at 100° C. The product obtained (1.13 g) is dissolved in 115 ml of dimethyl sulphoxide and, after addition of 0.1 g of decolorizing charcoal, the solution is filtered and the filter is then washed twice with 30 ml in total of dimethyl sulphoxide. The filtrate and the washings are combined, 115 ml of distilled water are added and they are centrifuged. The solid is suspended in 20 ml of distilled water, filtered, washed twice with 20 ml in total of acetone and dried under reduced pressure (1 mmHg; 0.13 kPa) at 100° C. 1 g of 5H,10H-imidazo[1,2-a]indeno[1,2-e]pyrazine-4,10-dione is thus obtained, in the form of a red-orange solid melting at 360° C. (decomposition) [N.M.R. spectrum: (200 MHz; DMSO $d_6$; d in ppm): 7.42 and 7.55 (2t, J=7 Hz, 2H: —H7 and —H8); 7.52 and 7.72 (2d, J=7 Hz, 1H each: —H6 and —H9); 7.62 and 8.13 (2d, J=1 Hz, 1H each: —H of the imidazole); 13.60 (cplx, 1H: —NH—)].

EXAMPLE 3

0.86 g of sodium borohydride is added over 5 minutes to a stirred suspension of 2.4 g of 5H,10H-imidazo[1,2-a]indeno[1,2-e]pyrazine-4,10-dione in 75 ml of methanol at a temperature between 25° C. and 35° C. After stirring for 30 minutes at 20° C., the insoluble material is isolated by filtration, washed with 10 ml of methanol and dried under reduced pressure (15 mmHg; 2 kPa) at 20° C. The product obtained (2.3 g) is dissolved in 100 ml of dimethylformamide and, after addition of 0.1 g of decolorizing charcoal, the solution is filtered and the filter is then washed with 20 ml of dimethylformamide. The filtrate and the washings are combined and 240 ml of distilled water are added. The solid is filtered off, washed twice with 40 ml in total of distilled water and with 20 ml of acetone and then dried under reduced pressure (1 mmHg; 0.13 kPa) at 100° C. 1.9 g of 10-hydroxy-5H,10H-imidazo-[1,2-a]indeno[1,2-e]pyrazin-4-one are thus obtained, melting at 290° C. (decomposition) [N.M.R. spectrum: (200 MHz; DMSO $d_6$; δ in ppm): 5.65 (d, J=8.5 Hz, 1H: CH—O—); 6.17 (d, J=8.5 Hz, 1H: —OH); 7.33 and 7.41 (2dt, J=7.5 and 1 Hz, 1H each: —H7 and —H8); 7.57 and 7.77 (2dd, J=7.5 and 1 Hz, 1H each: —H6 and —H9); 7.58 and 7.93 (2s broad, 1H each: —H of the imidazole); 12.40 (cplx, 1H: —NH—)].

EXAMPLE 4

A suspension of 5.25 g of 10-(E-hydroxy-imino)-5H,10H-imidazo[1,2-a]indeno[1,2-e]pyrazin-4-one and 2.9 g of zinc powder in 100 ml of acetic acid is heated for 2 hours at a temperature between 80° C. and 90° C. After addition of 100 ml of acetic acid, the mixture is filtered and the filtrate is concentrated to dryness under reduced pressure (10 mmHg; 2 kPa) at 65° C. The product obtained (3.8 g) is suspended in 100 ml of distilled water, filtered, washed with 10 ml of distilled water and with 10 ml of acetone and then dried under reduced pressure (15 mmHg; 2 kPa) at 20° C. The product obtained (2 g) is dissolved in 60 ml of boiling dimethylformamide and, after addition of 0.1 g of decolorizing charcoal, the solution is filtered while hot. The filter is washed with 10 ml of boiling dimethylformamide and the filtrate and the combined washings are then stored for 4 hours at a temperature in the region of 20° C. The crystals formed are separated out by filtration, washed successively with 10 ml of dimethylformamide, 10 ml of distilled water and 10 ml of acetone and dried to dryness under reduced pressure (1 mmHg; 0.13 kPa) at 100° C. 0.43 g of 10-acetamido-5H,10H-imidazo[1,2-a]indeno[1,2-e]pyrazin-4-one is thus obtained, decomposing without melting at 330° C. [N.M.R. spectrum: (200 MHz; DMSO $d_6$; δ in ppm): 2.00 (s, 3H: —CO—$CH_3$); 6.13 (d, J=8.5 Hz, 1H: CH—N); 7.35 and 7.48 (2t, J=7.5 Hz, 1H each: —H7 and —H8); 7.48 and 7.85 (2d, J=7.5 Hz, 1H each: —H6 and —H9); 7.58 and 7.65 (2s broad, 1H each: —H of the imidazole); 8.58 (d, J=8.5 Hz, 1H: —NH—$COCH_3$); 12.50 (cplx, 1H: —NH—)].

EXAMPLE 5

A solution of 12.9 g of 10-acetamido-5H,10H-imidazo[1,2-a]indeno[1,2-e]pyrazin-4-one in 650 ml of 2N aqueous hydrochloric acid solution is heated to boiling for 2 hours, cooled and then concentrated to dryness under reduced pressure (15 mmHg; 2 kPa) at 80° C. 4 g (of the 14.8 g obtained in total) are dissolved in 250 ml of distilled water and the solution is stirred for 16 hours at a temperature in the region of 20° C. The crystals formed are separated out by filtration, washed successively with 25 ml of distilled water and 25 ml of methanol and then air-dried at a temperature in the region of 20° C. The product obtained (3.5 g) is stirred in suspension for 10 minutes in 100 ml of boiling methanol and, after cooling and storing for 1 hour at 5° C., is isolated by filtration, washed with 20 ml of chilled methanol and then dried under reduced pressure (1 mmHg; 0.13 kPa) at 100° C. 2.1 g of 10-amino-5H,10H-imidazo[1,2-a]indeno[1,2-e]-pyrazin-4-one hydrochloride are thus obtained, decomposing without melting at about 240° C. [N.M.R. spectrum: (200 MHz; DMSO $d_6$; δ in ppm): 5.70 (broad s, 1H: CH—$N^+$—$Cl^-$); 7.48 and 7.58 (2t, J=7.5 Hz, 1H each: —H7 and —H8); 7.72 and 8.76 (2s, 1H each: —H of the imidazole); 7.98 and 8.09 (2d, J=7.5 Hz, 1H each: —H6 and —H9); 9.47 (cplx, 3H: $N^+H_3Cl^-$); 12.80 (cplx, 1H: —NH—)].

EXAMPLE 6

6.3 g of t-butoxybis(dimethylamino)methane are added dropwise over 5 minutes at a temperature in the region of 25° C. to a suspension of 5.5 g of 5H,10H-imidazo[1,2-a]indeno[1,2-e]pyrazin-4-one in 100 ml of dimethylformamide. After stirring for 30 minutes at the same temperature, the mixture is poured into 500 ml of distilled water and extracted 5 times with 1.5 litres in total of chloroform. The organic extracts are combined, washed with 250 ml of distilled water, dried over anhydrous magnesium sulphate and concentrated to dryness under reduced pressure (15 mmHg; 2 kPa) at 60° C. The product obtained (4.5 g) is suspended in 25 ml of methanol, filtered, washed twice with 20 ml in total of methanol and dried under reduced pressure (15 mmHg; 2 kPa) at 20° C. The product obtained (4.5 g) is dissolved in 45 ml of boiling dimethylformamide and, after cooling, the solution is stored for 4 hours at a temperature in the region of 5° C. The crystals are separated out by filtration, washed successively with 10 ml of dimethylformamide, 10 ml of acetone and dried to dryness under reduced pressure (1 mmHg; 0.13 kPa) at 100° C. 4 g of 10-[(E)-dimethylaminomethylene]-5H,10H-imidazo[1,2-a]indeno[1,2-e]pyrazin-4-one are thus obtained, melting at 293° C. [N.M.R. spectrum: (200 MHz; DMSO $d_6$; δ in ppm): 3.35 (s, 6H: —N($CH_3$)$_2$); 7.18 and 7.28 (2t, J=7.5 Hz, 2H: —H7 and —H8); 7.48 and 7.92 (2d, J=7.5 Hz, 1H each: —H6 and —H9); 7.63 and 8.50 (2s broad, 1H each: —H of the imidazole); 8.09 (s, 1H: =CH—N); 12.30 (cplx, 1H: —NH—)].

EXAMPLE 7

A solution of 1.4 g of 10-dimethylaminomethylene-5H,10H-imidazo[1,2-a]indeno[1,2-e]pyrazin-4-one in 35 ml of 5N hydrochloric acid is stirred for 30 minutes at a temperature in the region of 25° C. After addition of 60 ml of distilled water and neutralization with 120 ml of saturated aqueous sodium hydrogen carbonate solution, the solid formed is separated out by filtration, washed twice with 60 ml in total of distilled water and air-dried. The product obtained (1.1 g) is dissolved in 120 ml of dimethyl sulphoxide and, after addition of 120 ml of distilled water, the solid formed is separated out by filtration, washed twice with 10 ml in total of distilled water and twice with 10 ml in total of acetone and then dried under reduced pressure (1 mmHg; 0.13 kPa) at 100° C. 1 g of 10-hydroxymethylene-5H,10H-imidazo[1,2-a]indeno-[1,2-e]pyrazin-4-one is thus obtained as a 60/40 mixture of the Z and E forms, decomposing without melting at 290° C. [N.M.R. spectrum: (200 MHz; DMSO $d_6$; δ in ppm): a 60/40 mixture of isomers is observed: from 7.20 to 7.40 (mt, 2H: —H7 and —H8); 7.56 and 7.64–8.29 and 8.79 (4s broad, twice 1H: —H of the imidazole); from 7.80 to 8.15 (mt, 2H: —H6 and —H9); 8.21 and 8.24 (2s, 1H in total: =CH—O—); 12.43 (cplx, 1H: —NH—)].

EXAMPLE 8

A solution of 2 g of 5H,10H-imidazo[1,2-a]-indeno[1,2-e]pyrazin-4-one in 50 ml of anhydrous dimethyl sulphoxide is stirred with 4 g of sodium hydroxide pellets and 50 mg of tetrabutylammonium bromide for 1 hour at a temperature in the region of 20° C. 0.87 ml of methyl iodide is then added dropwise and the stirring is continued for 6 hours. The reaction mixture is then poured into 300 g of water and ice, acidified to pH 1 with 1N hydrochloric acid and extracted with 3 times 100 ml of chloroform. The organic phase is washed with 100 ml of water, filtered, dried over magnesium sulphate and concentrated on a rotary evaporator. The black oil obtained (2.8 g) is purified by chromatography on a column of silica (250 g) with a mixture of ethyl acetate and methanol (95/5 by volume) and the coloured solid obtained (0.5 g) is triturated with 20 ml of acetone, filtered, washed with a mixture of 10 ml of ethyl acetate and 1 ml of ethanol and dried at 50° C. to give 0.2 g of 5H,10H-10,10-dimethylimidazo[1,2-a]indeno[1,2-e]-pyrazin-4-one in the form of a cream-coloured solid melting above 260° C. (Analysis % calculated C: 71.70, H: 5.21, N: 16.72, O: 6.37, % found C: 71.7, H: 5.3, N: 16.4, O: 6.4).

EXAMPLE 9

A suspension of 1.3 g of 5H,10H-imidazo-[1,2-a]indeno[1,2-e]pyrazin-4-one, 2 g of sodium hydroxide pellets and 32 mg of tetrabutylammonium bromide in 10 ml of dry dimethyl sulphoxide is stirred at a temperature in the region of 18° C. A solution of 0.4 ml of 1,2-dibromoethane in 5 ml of dimethyl sulphoxide is then added and the stirring is continued overnight at a temperature in the region of 20° C. The reaction mixture is poured into a mixture of water and ice (250 ml), acidified with 8 ml of acetic acid and kept stirring for 1 hour 30 minutes. The solid formed is then filtered off and it is purified by chromatography on a column of silica (100 g) with a mixture of dichloromethane and methanol (95/5 by volume). After drying at 60° C., 0.45 g of spiro[5H,10H-imidazo[1,2-a]indeno[1,2-e]pyrazine-10:1'-cyclopropane]-4-one is obtained, in the form of a pink solid melting above 260° C. (Analysis % calculated C: 72.28, H: 4.45, N: 16.86, O: 6.42, % found C: 71.8, H: 4.4, N: 16.3).

EXAMPLE 10

The procedure is performed as in Example 9, but starting with 1.1 g of 5H,10H-imidazo[1,2-a]indeno-[1,2-e]pyrazin-4-one, 40 ml of dimethyl sulphoxide, 2 g of sodium hydroxide pellets, 32 mg of tetrabutylammonium bromide and 0.6 ml of 1,4-dibromobutane. After drying at 80° C., 0.17 g of spiro[5H,10H-imidazo[1,2-a]indeno[1,2-e]pyrazine-10:1'-cyclopentane]-4-one is obtained, in the form of a white solid melting above 260° C. (Analysis % calculated C: 73.63, H: 5.45, N: 15.15, O: 5.77, % found C: 73.8, H: 5.8, N: 15.1, O: 6.0).

EXAMPLE 11

A mixture of 1 g of 10-hydroxymethylene-5H,10H-imidazo[1,2-a]indeno[1,2-e]pyrazin-4-one, 80 ml of dimethylformamide and 20 ml of methanol is hydrogenated at a temperature in the region of 20° C. and at normal pressure for 4 hours in the presence of 10% palladium on charcoal. After filtration of the catalyst under inert atmosphere, the solvents are evaporated off and the beige solid obtained (1.25 g) is purified by chromatography on a column of silica (100 g) with a mixture of dichloromethane and methanol (95/5 by volume). After drying at 90° C., 0.35 g of 10-methyl-5H,10H-imidazo[1,2-a]indeno[1,2-e]pyrazin-4-one is obtained, in the form of a cream-coloured solid melting above 260° C. (Analysis % calculated C: 70.87, H: 4.67, N: 17.71, O: 6.74, % found C: 70.5, H: 4.4, N: 17.4).

EXAMPLE 12

To a solution of 0.45 g of 5H,10H-imidazo-[1,2-a]indeno [1,2-e]pyrazin-4-one in 20 ml of dimethyl sulphoxide under nitrogen are added, at a temperature in the region of 20° C. and with stirring, 60 mg of sodium hydride. The stirring is continued for 2 hours and a further 66 mg of sodium hydride are then added. The reaction medium is heated to 45° C. for 30 minutes, cooled to 20° C. and 0.25 ml of benzyl bromide are added. After continuing the stirring for 3 hours, the reaction mixture is poured into 150 ml of water, acidified to pH 4 with acetic acid and extracted with three times 60 ml of chloroform. The organic phases are combined, washed with twice 100 ml of water, dried over magnesium sulphate, filtered and concentrated on a rotary evaporator. The black solid obtained (0.78 g) is purified by chromatography on a column of silica (70 g) with a mixture of dichloromethane and methanol (95/5 by volume) to give 0.1 g of 10,10-dibenzyl-5H,10H-imidazo-[1,2-a]indeno[1,2-e]pyrazin-4-one in the form of a pale green solid melting above 260° C. [N.M.R. spectrum: (200 MHz; DMSO $d_6$; δ in ppm): 3.63 and 3.85 (2d, J=14 Hz, 2H each: —CH$_2$—Ar); 6.36 (d, J=7 Hz, 4H: ortho-H of the benzyls); from 6.75 to 6.95 (mt, 6H: meta-H and para-H of the benzyls); from 7.29 to 7.45 (2t, J=7.5 Hz, 1H each: —H$_7$ and —H$_8$); 7.82 and 8.80 (2s broad, 1H each: —H of the imidazole); 7.38 and 8.02 (2d, J=7.5 Hz, 1H each: —H6 and —H9); 11.9 (cplx, 1H: —NH—)].

EXAMPLE 13

A mixture of 0.4 g of 10-benzylidene-5H,10H-imidazo[1,2-a]indeno[1,2-e]pyrazin-4-one, 90 ml of dimethylformamide and 10 ml of methanol is hydrogenated at a temperature in the region of 20° C. at a pressure of 1.9 bar of hydrogen for 3 hours in the presence of 10% palladium on charcoal. The catalyst is then filtered off under inert atmosphere and the solvents are evaporated off. The brown solid obtained (0.37 g) is purified by chromatography on a column of silica (35 g) with a mixture of dichloromethane and methanol (90/10 by volume). After trituration with 5 ml of dichloromethane, filtration and drying at 100° C., 0.15 g of 10-benzyl-5H,10H-imidazo[1,2-a]indeno[1,2-e]pyrazin-4-one is obtained, in the form of a beige solid melting above 260° C. (Analysis % calculated C: 76.66, H: 4.82, N: 13.41, O: 5.11, % found C: 76.3, H: 4.6, N: 13.4).

EXAMPLE 14

A suspension of 5.75 g of 5H,10H-imidazo-[1,2-a]indeno [1,2-e]pyrazin-4-one, 10 g of sodium hydroxide pellets and 125 mg of tetrabutylammonium bromide in 200 ml of dimethyl sulphoxide is stirred at a temperature in the region of 20° C. 3.18 g of benzaldehyde are then added and the stirring is continued for 18 hours at a temperature in the region of 20° C. The reaction mixture is poured into a mixture of water and ice (250 ml) and acidified with 100 ml of acetic acid. The solid formed is filtered off and the crude product is purified by two successive chromatographies on a column of silica with a mixture of dichloromethane and methanol (90/10 by volume). 0.13 g of 10-benzylidene-5H,10H-imidazo[1,2-a]indeno-[1,2-e]pyrazin-4-one is thus obtained, in the form of a yellow solid melting above 260° C. (Analysis % calculated C: 77.16, H: 4.21, N: 13.50, O: 5.14, % found C: 76.7, H: 3.7, N: 13.2).

EXAMPLE 15

To a suspension of 3 g of 10-hydroxymethylene-5H,10H-imidazo[1,2-a]indeno[1,2-e]pyrazin-4-one (mixture of the Z and E forms) in 240 ml of methanol is added 1 g of sodium borohydride portionwise over 10 minutes with stirring, and the stirring is continued at a temperature in the region of 20° C. for 1 hour 30 minutes. A further 1 g of sodium borohydride is added portionwise and the stirring is continued for 30 minutes. The reaction mixture is then filtered and the filter is rinsed with twice 30 ml of methanol. The insoluble material is taken up with 50 ml of water and 4 ml of 1N hydrochloric acid, filtered again, washed with water until neutral and air-dried. The crude product (1 g) is purified by dissolution while hot in 65 ml of dimethylformamide, filtration, addition to the still hot filtrate of 80 ml of methanol and crystallization in an ice-water bath. The crystals obtained are filtered off, washed with twice 15 ml of methanol and dried at 80° C. 0.66 g of 10-hydroxymethyl-5H,10H-imidazo[1,2-a]indeno[1,2-e]pyrazin-4-one is thus obtained, in the form of a white solid melting above 260° C. (Analysis % calculated C: 66.40, H: 4.38, N: 16.59, O: 12.63, % found C: 66.4, H: 4.3, N: 16.6, O: 12.1).

EXAMPLE 16

2.8 g of a mixture of 10-(2-methyl-1-propenyl)-5H,10H-imidazo[1,2-]indeno[1,2-e]pyrazin-4-one and 10-(2-methylpropylidene)-5H,10H-imidazo-[1,2-a]indeno[1,2-e] pyrazin-4-one are hydrogenated in the presence of 180 ml of dimethylformamide, 20 ml of methanol and 0.5 g of 10% palladium on charcoal for 22 hours at 50° C. and at a pressure of 54 bar of hydrogen. After filtration of the catalyst under inert atmosphere, the solvents are evaporated off and the grey solid obtained (2.1 g) is purified by chromatography on a column of silica (180 g partially deactivated with 3 ml of water), using a mixture of dichloromethane and methanol (90/10 by volume) as eluent. After trituration in 20 ml of ethyl ether, filtration and drying at 100° C., 1.2 g of 10-isobutyl- 5H,10H-imidazo[1,2-a]indeno[1,2-e]pyrazin-4-one are thus obtained, in the form of a cream-coloured solid melting above 260° C. (Analysis % calculated C: 73.10, H: 6.13, N: 15.04, O: 5.73, % found C: 72.9, H: 5.6, N: 14.8).

The mixture of 10-(2-methyl-1-propenyl)-5H,10H-imidazo[1,2-a]indeno[1,2-e]pyrazin-4-one and 10-(2-methylpropylidene)-5H,10H-imidazo[1,2-a]indeno-[1,2-e]pyrazin-4-one can be prepared in the following way: the procedure is performed as in Example 14, but starting with 6 g of 5H,10H-imidazo[1,2-a]indeno-[1,2-e]pyrazin-4-one, 250 ml of dimethyl sulphoxide, 10 g of sodium hydroxide pellets, 125 mg of tetrabutylammonium bromide and 2.16 g of isobutyraldehyde. The crude product (6.26 g) is dissolved in 100 ml of dimethyl sulphoxide and decolorized at 60° C. with 0.6 g of 3S charcoal. After filtration, 250 ml of distilled water are added to the filtrate and the precipitate formed is drained and dried at 80° C. 4.3 g of a mixture of 10-(2-methyl-1-propenyl)-5H,10H-imidazo[1,2-a]indeno[1,2-e]pyrazin-4-one and 10-(2-methylpropylidene)-5H,10H-imidazo-[1,2-a]indeno[1,2-e]pyrazin-4-one are thus obtained, in the form of a green solid which is used as it is in the subsequent syntheses.

EXAMPLE 17

A mixture of 10-(2-furylmethylene)-5H,10H-imidazo[1,2-a]indeno[1,2-e]pyrazin-4-one, 100 ml of dimethylformamide and 0.15 g of 10% palladium on charcoal is hydrogenated by flushing with a stream of hydrogen at a temperature in the region of 20° C. for 2 hours. The catalyst is then filtered off under inert atmosphere and the solvent is evaporated off. The brown solid obtained (2 g) is purified by trituration in 50 ml of acetone, filtration and crystallization of the insoluble material obtained (1 g) in 80 ml of methanol. After filtration and drying at 80° C., 0.48 g of 10-(2-furylmethyl)-5H,10H-imidazo[1,2-a]indeno[1,2-e]-pyrazin-4-one is obtained, in the form of a light brown solid melting above 260° C. (Analysis % calculated C: 71.28, H: 4.32, N: 13.85, O: 10.55, % found C: 71.5, H: 4.2, N: 14.0).

10-(2-Furylmethylene)-5H,10H-imidazo[1,2-a]-indeno[1,2-e]pyrazin-4-one may be prepared in the following way: to a solution, cooled to 18° C., of 2 g of 5H,10H-imidazo [1,2-a]indeno[1,2-e]pyrazin-4-one in 30 ml of dimethyl sulphoxide is added 0.64 g of sodium hydride portionwise and with stirring. The stirring is continued for 35 minutes at a temperature in the region of 20° C. and a solution of 0.83 ml of 2-furaldehyde in 10 ml of dimethyl sulphoxide is then added dropwise. The stirring is continued for 2 hours. The reaction mixture is then poured into a mixture of water and ice (200 ml) and acidified at pH 4 with acetic acid. The coloured suspension obtained is centrifuged and the solid thus isolated is triturated in 50 ml of acetone, filtered and air-dried to give 2.17 g of 10-(2-furylmethylene)-5H,10H-imidazo[1,2-a]indeno-[1,2-e]pyrazin-4-one, in the form of an ochre solid melting above 260° C. which is used as it is in the subsequent syntheses.

EXAMPLE 18

The procedure is performed as in Example 13, but starting with 3.9 g of 10-(phenylpropylidene)-5H,10H-imidazo[1,2-a]indeno[1,2-e]pyrazin-4-one, 180 ml of dimethylformamide, 20 ml of methanol and 0.5 g of 10% palladium on charcoal. The crude product (3.8 g) is purified by chromatography on a column of silica (380 g partially deactivated with 10 ml of water), eluting with a mixture of dichloromethane and methanol (90/10 by volume). After trituration in 10 ml of dichloromethane, filtration and drying at 100° C., 1.1 g of 10-(phenylpropyl)-5H,10H-imidazo[1,2-a]indeno-[1,2-e]pyrazin-4-one are obtained, in the form of a beige solid melting at 232° C.

10-(Phenylpropylidene)-5H,10H-imidazo[1,2-a]-indeno[1,2-e]pyrazin-4-one may be prepared in the following way: the procedure is performed as in Example 14, but starting with 6 g of 5H,10H-imidazo-[1,2-a]indeno[1,2-e]pyrazin-4-one, 240 ml of dimethyl sulphoxide, 10 g of sodium hydroxide pellets, 125 mg of tetrabutylammonium bromide and 4.0 g of phenylpropionaldehyde. The crude product (7.2 g) is purified by crystallization in 140 ml of dimethyl sulphoxide and 140 ml of water to give 5.5 g of 10-(phenylpropylidene)-5H,10H-imidazo[1,2-a]indeno-[1,2-e]pyrazin-4-one, in the form of a yellow solid which is used as it is in the subsequent syntheses.

EXAMPLE 19

1.3 g of 10-hexylidene-5H,10H-imidazo[1,2-a]-indeno[1,2-e]pyrazin-4-one are hydrogenated at a temperature in the region of 20° C. and at a pressure of 9.4 bar of hydrogen in the presence of 120 ml of dimethylformamide, 20 ml of methanol and 0.3 g of 10% palladium on charcoal for 17 hours. After filtration of the catalyst under inert atmosphere, the solvents are evaporated off and the crude product (1.2 g) is purified by chromatography on a column of silica (120 g partially deactivated with 2 ml of water), eluting with a mixture of dichloromethane and methanol (90/10 by volume). 0.47 g of 10-hexyl-5H,10H-imidazo[1,2-a]-indeno [1,2-e]pyrazin-4-one is thus obtained, in the form of a beige solid melting at about 185° C. (Analysis % calculated C: 74.24, H: 6.89, N: 13.67, O: 5.20, % found C: 74.3, H: 7.0, N: 13.6).

10—Hexylidene-5H,10H-imidazo[1,2-a]indeno-[1,2-e] pyrazin-4-one may be prepared in the following way: the procedure is performed as in Example 17 for the preparation of 10-(2-furylmethylene)-5H,10H-imidazo[1,2-a]indeno[1, 2-e]pyrazin-4-one, but starting with 2.23 g of 5H,10H-imidazo[1,2-a]indeno[1,2-e]-pyrazin-4-one, 50 ml of dimethyl sulphoxide, 0.72 g of sodium hydride and 1.1 g of hexanal. The crude product is purified by crystallization in 120 ml of dimethyl sulphoxide and 120 ml of water to give 1.3 g of 10-hexylidene-5H,10H-imidazo[1,2-a]indeno[1,2-e]-pyrazin-4-one, in the form of a yellow solid which is used as it is in the subsequent syntheses.

EXAMPLE 20

The procedure is performed as in Example 17 for the preparation of 10-(2-furylmethylene)-5H,10H-imidazo[1,2-a]indeno[1,2-e]pyrazin-4-one, but starting with 2 g of 5H,10H-imidazo[1,2-a]indeno[1,2-e]pyrazin-4-one, 40 ml of dimethyl sulphoxide, 0.64 g of sodium hydride and 1.07 g of 4-pyridinecarboxaldehyde. The crude product (1.5 g) is purified by crystallization in 100 ml of dimethylformamide and 50 ml of methanol to give 1.06 g of 10-(4-pyridylmethylene)-5H,10H-imidazo-[1,2-a]indeno[1,2-e] pyrazin-4-one, in the form of an orange solid melting above 260° C. (Analysis % calculated C: 73.07, H: 3.87, N: 17.94, O: 5.12, % found C: 72.9, H: 3.7, N: 18.2).

EXAMPLE 21

The procedure is performed as in Example 13, but starting with 0.8 g of 10-(4-pyridylmethylene)-5H,10H-imidazo[1, 2-a]indeno[1,2-e]pyrazin-4-one, 250 ml of dimethylformamide and 80 mg of 10% palladium on charcoal, with addition also of 10 ml of acetic acid. 0.2 g of 10-(4-pyridylmethyl)-5H,10H-imidazo[1,2-a]-indeno[1,2-e]pyrazin-4-one is obtained, in the form of a pale yellow solid melting above 260° C. (Analysis % calculated C: 72.60, H: 4.49, N: 17.82, O: 5.09, % found C: 72.3, H: 4.3, N: 17.8).

EXAMPLE 22

The procedure is performed as in Example 17 for the preparation of 10-(2-furylmethylene)-5H,10H-imidazo[1,2-a]indeno[1,2-e]pyrazin-4-one, but starting with 3 g of 5H,10H-imidazo[1,2-a]indeno[1,2-e]pyrazin-4-one, 60 ml of dimethyl sulphoxide, 0.96 g of sodium hydride and 1.6 g of 3-pyridinecarboxaldehyde. 1.38 g of 10-(3-pyridylmethylene)-5H,10H-imidazo[1,2-a]indeno-[1,2-e]pyrazin-4-one are obtained, in the form of a yellow-orange solid melting above 260° C. (Analysis % calculated C: 73.07, H: 3.87, N: 17.94, O: 5.12, % found C: 73.1, H: 3.9, N: 17.9, O: 5.1).

EXAMPLE 23

The procedure is performed as in Example 21, but starting with 1 g of 10-(3-pyridylmethylene)-5H,10H-imidazo[1,2-a]indeno[1,2-e]pyrazin-4-one, 150 ml of dimethylformamide, 5 ml of acetic acid and 0.1 g of 10% palladium on charcoal. 0.38 g of 10-(3-pyridylmethyl)-5H,10H-imidazo[1,2-a]indeno-[1,2-e]pyrazin-4-one is obtained, in the form of an off-white solid melting above 260° C. (Analysis % calculated C: 72.60, H: 4.49, N: 17.82, O: 5.09, % found C: 72.3, H: 4.8, N: 17.8, O: 5.4).

EXAMPLE 24

The procedure is performed as in Example 21, but starting with 0.7 g of 10-(2-pyridylmethylene)-5H,10H-imidazo[1,2-a]indeno[1,2-e]pyrazin-4-one, 200 ml of dimethylformamide, 5 ml of acetic acid and 70 mg of 10% palladium on charcoal. The crude product (1.1 g) is purified by trituration in a mixture of 10 ml of dichloromethane and 40 ml of ethyl ether, followed by crystallization in 25 ml of dimethylformamide and 40 ml of water. 0.35 g of 10-(2-pyridylmethyl)-5H,10H-imidazo[1,2-a]indeno[1,2-e]pyrazin-4-one is obtained, in the form of a light beige solid melting above 260° C. (Analysis % calculated C: 72.60, H: 4.49, N: 17.82, O: 5.09, % found C: 72.5, H: 4.6, N: 17.9, O: 5.5).

10-(2-Pyridylmethylene)-5H,10H-imidazo-[1,2-a]indeno[1,2-e]pyrazin-4-one may be prepared in the following way: the procedure is performed as in Example 17 for the preparation of 10-(2-furylmethylene)-5H,10H-imidazo[1,2-a]indeno[1,2-e]pyrazin-4-one, but starting with 3 g of 5H,10H-imidazo[1,2-a]-indeno[1,2-e]pyrazin-4-one, 60 ml of dimethyl sulphoxide, 0.96 g of sodium hydride and 1.6 g of 2-pyridinecarboxaldehyde. 0.7 g of 10-(2-pyridylmethylene)-5H,10H-imidazo[1,2-a]indeno[1,2-e]pyrazin-4-one is obtained, in the form of an orange solid which is used as it is in the subsequent syntheses.

EXAMPLE 25

The procedure is performed as in Example 21, but starting with 1.65 g of 10-(2-imidazolylmethylene)-5H,10H-imidazo[1,2-a]indeno[1,2-e]pyrazin-4-one, 300 ml of dimethylformamide, 5 ml of acetic acid and 0.17 g of 10% palladium on charcoal. 0.5 g of 10-(2-imidazolylmethyl)-5H,10H-imidazo[1,2-a]indeno-[1,2-e]pyrazin-4-one is obtained, in the form of a pale yellow solid melting above 260° C. (Analysis % calculated C: 67.32, H: 4.32, N: 23.09, O: 5.27, % found C: 67.2, H: 4.3, N: 23.0).

10-(2-Imidazolylmethylene)-5H,10H-imidazo-[1,2-a]indeno[1,2-e]pyrazin-4-one may be prepared in the following way: the procedure is performed as in Example 17 for the preparation of 10-(2-furylmethylene)-5H,10H-imidazo[1,2-a]indeno[1,2-e]pyrazin-4-one, but starting with 3 g of 5H,10H-imidazo[1,2-a]-indeno[1,2-e]pyrazin-4-one, 70 ml of dimethyl sulphoxide, 1.4 g of sodium hydride and 1.44 g of 2-imidazolecarboxaldehyde. 1.65 g of 10-(2-imidazolylmethylene)-5H,10H-imidazo[1,2-a]indeno[1,2-e]pyrazin-4-one are obtained, in the form of a dark green solid which is used as it is in the subsequent syntheses.

EXAMPLE 26

1.8 g of sodium hydride are added at 20° C. to a solution of 7.4 g of 10-(hydroxyimino)-5H,10H-imidazo[1,2-a]indeno[1,2-e]pyrazin-4-one (85/15 mixture of the E and Z forms) (crude product before purification obtained in Example 1) in 125 ml of anhydrous dimethyl sulphoxide, maintained under a nitrogen atmosphere. After stirring for 30 minutes, a solution of 5.4 g of t-butyl bromoacetate in 10 ml of anhydrous dimethyl sulphoxide is added dropwise over 5 minutes at the same temperature. The mixture is stirred for 1 hour, poured into 1,200 g in total of ice and distilled water and centrifuged. After removal of the supernatant solution, the insoluble material is isolated by filtration, washed with 50 ml of distilled water and twice with 125 ml in total of methanol and then air-dried. The product obtained (6.4 g) is dissolved at 20° C. in 800 ml of dimethylformamide and, after addition of decolorizing charcoal, the solution is filtered. The filter is washed with 100 ml of dimethylformamide and the filtrate and the washings are then combined and poured into 1,800 ml of distilled water. After centrifugation, filtration of the insoluble material, washing with 20 ml of distilled water and 20 ml of methanol and then drying under reduced pressure (1 mmHg; 0.13 kPa) at 100° C., 5 g of tert-butyl 10-(4-oxo-5H,10H-imidazo[1,2-a]indeno-[1,2-e]pyrazinylidene) aminooxyacetate are obtained, melting at 305° C. (decomposition) [N.M.R. spectrum: (300 MHz; DMSO $d_6$; δ in ppm): mixture of isomers: 85% E isomer, 15% Z isomer: 1.47 (s, 9H: —C(CH$_3$)$_3$); 4.97 and 5.02 (2s, 2H in total, =N—OCH$_2$ of the E and Z isomer respectively); from 7.30 to 7.50 (mt, 2H: —H7 and —H8); 7.60 (s, 1H: —H of the imidazole); from 7.70 to 7.90 and 8.12 (mt and (d, J=7.5 Hz), 1H each: —H6 and —H9); 7.94 and 8.52 (2s, 1H in total: the other —H of the imidazole of the E and Z isomer respectively); 12.77 (cplx, 1H: CO—NH—)].

EXAMPLE 27

1.7 g of benzoyl chloride are added over 1 minute to a solution of 3.1 g of 10-amino-5H,10H-imidazo[1,2-a]indeno [1,2-e]pyrazin-4-one hydrochloride in 200 ml of 0.1N sodium hydroxide. The mixture is stirred for 2 hours at a temperature in the region of 20° C. and the insoluble material is separated out by filtration, washed twice with 200 ml in total of distilled water and air-dried. The product obtained (3 g) is dissolved in 100 ml of dimethyl sulphoxide and, after addition of decolorizing charcoal, the solution is filtered. The filter is washed with 20 ml of dimethyl sulphoxide and the filtrate and the washings are then combined and 80 ml of distilled water are added at 20° C. The insoluble material is separated out by filtration, washed twice with 50 ml in total of distilled water and with 25 ml of acetone and then dried under reduced pressure (1 mmHg; 0.13 kPa) at 100° C. 1.75 g of 10-benzamido-5H,10H-imidazo[1,2-a]-indeno[1,2-e]pyrazin-4-one are thus obtained, decomposing without melting at 300° C. [N.M.R. spectrum: (200 MHz; DMSO d$_6$; δ in ppm): 6.40 (d, J=8.5 Hz, 1H: CH—N); from 7.30 to 7.70 (mt, 8H: —H6, —H7, —H8, —H9, aromatic —H para and meta to the —CO—NH— and —H of the imidazole); from 7.80 to 8.00 (mt, 3H: aromatic —H ortho to the —CO—NH— and —H of the imidazole); 9.14 (d, J=8.5 Hz, 1H: —NH—); 12.55 (cplx, 1H: —CO—NH— of the ring)].

EXAMPLE 28

To a suspension of 4 g of 5H,10H-imidazo-[1,2-a]indeno [1,2-e]pyrazin-4-one in 70 ml of dimethyl sulphoxide are added, with stirring and under cover of nitrogen, 3.9 g of 2-pyrazinecarboxaldehyde and, after cooling to 19° C., 1.6 g of 60% sodium hydride are added portionwise while maintaining the reaction medium at a temperature between 15° and 21° C. The stirring is continued for 4 hours and then 70 ml of water, 5 ml of acetic acid and 50 ml of methanol are successively added dropwise at a temperature in the region of 20° C. The suspension obtained is filtered and the solid thus isolated is washed with methanol, air-dried and triturated in a mixture of 80 ml of dimethylformamide and 25 ml of methanol. After drying at 60° C. under vacuum (1 mmHg; 0.13 kPa) 3.3 g of 10-(2-pyrazinylmethylene)-5H, 10H-imidazo[1,2-a]indeno[1,2-e]pyrazin-4-one are obtained, in the form of a red-orange solid melting above 260° C. (Analysis % calculated C: 69.00, H: 3.54, N: 22.35, O: 5.11, % found C: 69.6, H: 3.6, N: 22.0, O: 4.9).

2-Pyrazinecarboxaldehyde may be prepared according to the process described by H. Rutner and P. E. Spoerri, J. Org. Chem., 28, 1898 (1963).

EXAMPLE 29

A mixture of 3.2 g of 10-(2-pyrazinylmethylene-5H,10H-imidazo[1,2-a]indeno[1,2-e]pyrazin- 4-one, 250 ml of dimethylformamide, 50 ml of methanol and 5 ml of acetic acid is hydrogenated at a temperature in the region of 20° C. and a pressure of 1.8 bar of hydrogen, in the presence of 10% palladium on charcoal for 18 hours. The catalyst is filtered off under inert atmosphere and the filtrate is concentrated on a rotary evaporator. On addition of 200 ml of methanol a precipitate is formed which, after trituration in dichloromethane (100 ml), filtration and drying at 60° C. under vacuum (1 mmHg; 0.13 kPa), gives 1.4 g of 10-(2-pyrazinylmethyl)-5H,10H-imidazo[1,2-a]-indeno[1,2-e] pyrazin-4-one in the form of a beige solid melting above 260° C. (Analysis % calculated C: 68.56, H: 4.16, N: 22.21, O: 5.07, % found C: 68.3, H: 3.9, N: 21.9).

EXAMPLE 30

The procedure is performed as in Example 28, but starting with 3 g of 5H,10H-imidazo[1,2-a]indeno-[1,2-e]pyrazin-4-one, 60 ml of dimethyl sulphoxide, 0.96 g of 80% sodium hydride and 3.18 g of 4-quinolincarboxaldehyde. After treating with water and acetic acid, the suspension obtained is filtered and the solid thus isolated is washed with 2×30 ml of water and then 4×30 ml of acetone and dried at 100° C. under vacuum (2 mmHg; 0.26 kPa). 3.9 g of 10-(4-quinolylmethylene)-5H,10H-imidazo[1,2-a]indeno-[1,2-e] pyrazin-4-one are obtained, in the form of an orange solid melting above 260° C. (Analysis % calculated C: 76.23, H: 3.89, N: 15.46, O: 4.41, % found C: 75.9, H: 4.2, N: 15.4).

EXAMPLE 31

The procedure is performed as in Example 29, but starting with 3 g of 10-(4-quinolylmethylene)-5H,10H-imidazo[1,2-a]indeno[1,2-e]pyrazin-4-one, 130 ml of dimethylformamide, 130 ml of acetic acid and 0.3 g of 10% palladium on charcoal at a pressure of 15 bar of hydrogen for 22 hours. After removal of the catalyst and the solvents, a yellow-brown solid (3.1 g) is obtained which is treated with a mixture of acetic acid and dimethylformamide and filtered. 7 g of silica are added to the filtrate, which is concentrated on a rotary evaporator and purified by chromatograophy on a column of silica (250 g partially deactivated with 2% water), eluting with a mixture of dichloromethane and methanol (90/10 by volume). After drying at 90° C. under vacuum (2 mmHg; 0.26 kPa), 0.97 g of 10-(4-quinolylmethyl)-5H,10H-imidazo[1,2-a]indeno[1,2-e] pyrazin-4-one is obtained, in the form of a yellow solid melting above 260° C. (Analysis % calculated C: 75.81, H: 4.43, N: 15.37, O: 4.39, % found C: 75.4, H: 3.6, N: 15.2).

EXAMPLE 32

A mixture of 1.5 g of 10-(4-pyridylmethyl)-5H,10H-imidazo[1,2-a]indeno[1,2-e]pyrazin-4-one, 100 ml of acetic acid, 5 ml of 1N hydrochloric acid and 0.19 g of platinum oxide is hydrogenated at a pressure of 56 bar for 18 hours at 50° C. After removal of the catalyst and the solvent a beige solid (1.5 g) is obtained, to which is added 100 ml of water; the suspension obtained is washed with 50 ml of dichloromethane, basified to pH 8 with saturated sodium hydrogen carbonate solution, washed again with twice 50 ml of dichloromethane and concentrated on a rotary evaporator. 250 ml of dimethylformamide, 20 ml of water and 3 g of silica are added to the residue obtained and the mixture is concentrated on a rotary evaporator. The evaporation residue is purified by chromatography on a column of silica (150 g partially deactivated with 3% water), eluting with a mixture of chloroform, methanol and 28% aqueous ammonia (24/6/1 by volume). 0.18 g of 10-(4-piperidylmethyl)-5H,10H-imidazo[1,2-a]indeno-[1,2-e]pyrazin-4-one is obtained, in the form of an orange solid [N.M.R. spectrum: (300 MHz; (CD$_3$)$_2$SO d$_6$ with a few drops of CD$_3$COOD d$_4$; δ in ppm): from 1.10 to 1.50 (mt, 5H: CH$_2$ and CH of the piperidine); 2.05 to 2.35 (mt, 2H: CH$_2$); 2.65 (mt, 2H: NCH$_2$ of the piperidine axial H); 3.05 (broad d, J=12 Hz, 2H: NCH$_2$ of the piperidine equatorial H); 4.30 (dd, J=9 and 3 Hz, 1H: H10); 7.30 and 7.40 (2t, J=8.5 Hz, 2H: H7 and H8); 7.62 and 7.88 (2d broad, J=8.5 Hz, 1H each: H6 and H9); 7.58 and 8.02 (2s broad, 1H each: —H of the imidazole)].

EXAMPLE 33

To a suspension, cooled to 0° C., of 0.56 g of 10-carboxymethyl-5H,10H-imidazo[1,2-a]indeno[1,2-e]-pyrazin-4-one and 20 ml of chloroform is added, with stirring and under cover of argon, 0.21 ml of oxalyl chloride, followed by a mixture of 5 ml of chloroform and 0.5 ml of dimethylformamide. The stirring is continued for 4 hours at a temperature in the region of 20° C. and a solution of 0.38 g of sodium borohydride in 20 ml of dimethylformamide is added very slowly while maintaining the temperature close to 20° C. The reaction mixture is poured into 10 ml of water and left to stand overnight. After separation of the phases by settling, the organic phase is evaporated to give 0.4 g of yellow product (fraction A); the aqueous phase is acidified to pH 1 with 0.1N hydrochloric acid and the precipitate formed is filtered off, washed with acetone and air-dried to give 0.2 g of white product (fraction B). Fractions A and B are combined, dissolved in a mixture of methanol and dimethylformamide and purified by chromatography on a column of silica (30 g), eluting with a mixture of dichloromethane and methanol (95/5 by volume). After drying at 60° C. under vacuum (1 mmHg; 0.13 kPa), 0.1 g of 10-(2-hydroxyethyl)-5H,10H-imidazo-[1,2-a]indeno[1,2-e]pyrazin-4-one is obtained, in the form of an off-white solid melting above 260° C. (Analysis % calculated C: 67.41, H: 4.90, N: 15.72, O: 11.97, % found C: 67.6, H: 4.9, N: 15.3).

10-(Carboxymethyl)-5H,10H-imidazo[1,2-a]-indeno[1,2-e]pyrazin-4-one may be prepared according to the following process: a mixture of 1 g of 10-(tert-butoxycarbonylmethyl)-5H,10H-imidazo[1,2-a]indeno-[1,2-e]pyrazin-4-one, 5 ml of dimethyl sulphoxide and 25 ml of 3N hydrochloric acid in ethyl ether is stirred for 107 hours at a temperature in the region of 20° C. under cover of argon. After concentration under reduced pressure, the residue is crystallized in 30 ml of acetone. The solid obtained is treated with 50 ml of water and 7 ml of saturated sodium hydrogen carbonate solution. It is extracted with dichloromethane (3 times 50 ml), the aqueous phase is filtered and the aqueous solution is acidified with 8 ml of 1N hydrochloric acid. The precipitate formed is filtered off, washed with water and dried at 80° C. under vacuum (1 mmHg; 0.13 kPa) to give 0.35 g of 10-(carboxymethyl)-5H,10H-imidazo[1,2-a]indeno[1,2-e]pyrazin-4-one, in the form of a greenish solid melting above 260° C. (Analysis % calculated C: 64.05, H: 3.94, N: 14.94, O: 17.06, % found C: 63.7, H: 3.2, N: 14.9).

10-(tert-Butoxycarbonylmethyl)-5H,10H-imidazo[1,2-a]indeno[1,2-e]pyrazin-4-one may be prepared in the following way: a suspension of 1.78 g of 10-(tert-butoxycarbonylmethylene)-5H,10H-imidazo-[1,2-a]indeno [1,2-e]pyrazin-4-one in 280 ml of dimethylformamide and 20 ml of methanol is hydrogenated in the presence of 0.18 g of 10% palladium on charcoal for 20 hours at 10 bar of hydrogen and at a temperature in the region of 20° C. After evaporation of the solvents, the beige solid obtained is purified by chromatography on a column of silica (180 g partially deactivated with 2% water), eluting with a mixture of dichloromethane and methanol (95/5 by volume). A white solid is obtained which is triturated in 10 ml of methyl tert-butyl ether, filtered and dried at 80° C. under vacuum. (2 mmHg; 0.26 kPa) to give 0.35 g of 10-(tert-butoxycarbonylmethyl)-5H,10H-imidazo[1,2-a]-indeno[1,2-e]pyrazin-4-one (Analysis % calculated C: 67.64, H: 5.68, N: 12.45, O: 14.23, % found C: 67.2, H: 6.0, N: 12.4, O: 14.5).

10-(tert-Butoxycarbonylmethylene)-5H,10H-imidazo[1,2-a]indeno[1,2-e]pyrazin-4-one [lacuna]: to a solution, cooled to 19° C. and under cover of nitrogen, of 9 g of 5H,10H-imidazo[1,2-a]indeno[1,2-e]pyrazin-4-one in 180 ml of dimethyl sulphoxide are added 4 g of 60% sodium hydroxide portionwise with stirring. The stirring is continued for 35 minutes and 7.8 g of tert-butyl glyoxylate are added dropwise. After stirring for 18 hours the reaction mixture is treated with 9 ml of acetic acid and 150 ml of water. The suspension is filtered and the insoluble material is washed with water (2×200 ml) and then with acetone (3×100 ml) and dried at 80° C. under reduced pressure. The crude product obtained (5.85 g) is heated to about 90°–10° C. in 300 ml of dimethylformamide and filtered immediately, and 150 ml of methanol and 200 ml of water are added to the filtrate, which is left in the ice compartment of a refrigerator overnight. The crystals formed are filtered off, washed with 20 ml of water and dried at 80° C. under vacuum (2 mmHg; 0.26 kPa) to give 3.4 g of 10-(tert-butoxycarbonylmethylene)-5H,10H-imidazo-[1,2-a]indeno [1,2-e]pyrazin-4-one, in the form of a red solid melting above 260° C. (Analysis % calculated C: 68.05, H: 5.11, N: 12.53, O: 14.31, % found C: 68.0, H: 5.6, N: 12.5, O: 14.3).

tert-Butyl glyoxylate may be prepared according to the process described by L. A. Carpino, J. Org. Chem., 29, 2820 (1964).

EXAMPLE 34

To a mixture, stirred and under cover of argon, of 0.48 g of 10-methyl-5H,10H-imidazo[1,2-a]-indeno[1,2-e]pyrazin-4-one, 5 ml of dimethyl sulphoxide and 0.14 g of 80% sodium hydride is added 0.23 ml of benzyl chloride. The stirring is continued for one hour and the reaction mixture is then acidified with 0.5 ml of acetic acid and poured into 25 ml of ice-water. A pale pink precipitate is formed which is filtered off, washed with 3×10 ml of water and air-dried. The crude product is purified by chromatography on a column of silica (25 g), eluting with a mixture of dichloromethane and methanol (95/5 by volume). After drying at 60° C. under vacuum (1 mmHg; 0.13 kPa) 0.29 g of 10-benzyl-10-methyl-5H,10H-imidazo[1,2-a]indeno-[1,2-e]pyrazin-4-one is obtained, in the form of a pale pink solid melting above 260° C. (Analysis % calculated C: 77.04, H: 5.23, N: 12.84, O: 4.89, % found C: 76.8, H: 5.8, N: 12.8).

EXAMPLE 35

To a stirred mixture of 0.48 g of 10-methyl-5H,10H-imidazo[1,2-a]indeno[1,2-e]pyrazin-4-one, 25 ml of dimethylformamide and 0.33 g of 80% sodium hydride is added 0.3 ml of trimethylchlorosilane at a temperature in the region of 20° C. and under cover of argon. The stirring is continued for one hour, followed by the addition of 0.07 g of 80% sodium hydride and the stirring is continued for 30 minutes. 0.36 g of 4-chloromethylpyridine hydrochloride is then added and the stirring is continued for 20 minutes. 2 ml of acetic acid are added to the reaction mixture, which is poured into 150 ml of ice-water and concentrated on a rotary evaporator. The evaporation residue is treated with 200 ml of ethyl acetate and filtered, and the filtrate is evaporated. The yellow-orange paste obtained is purified by chromatography on a column of silica (30 g), eluting with a mixture of dichloromethane and methanol (95/5 by volume). After trituration in 40 ml of ethyl ether, filtration and drying at 60° C. under vacuum (1 mmHg; 0.13 kPa), 0.18 g of 10-methyl-10-(4-pyridylmethyl)-5H,10H-imidazo-[1,2-a]indeno[1,2-e]pyrazin-4-one is obtained, in the form of a cream-coloured solid melting above 260° C. (Analysis % calculated C: 73.15, H: 4.91, N: 17.06, O: 4.87, % found C: 73.2, H: 5.1, N: 17.0).

EXAMPLE 36

A solution of 3.3 g of tert-butyl 10-(4-oxo-5H,10H-imidazo[1,2-a]indeno[1,2-e]pyrazinylidene)-aminooxyacetate in 60 ml of trifluoroacetic acid is maintained at 60° C. for 1 hour 30 minutes, cooled to 20° C. and concentrated to dryness under reduced pressure (15 mmHg; 2 kPa) at 60° C. The product obtained (5.7 g) is dissolved in 190 ml of saturated aqueous sodium hydrogen carbonate solution and the solution is filtered, extracted twice with 200 ml in total of dichloromethane, acidified with 15 ml of acetic acid and stirred for 16 hours at a temperature in the region of 20° C. The solid formed is separated out by filtration, washed with 25 ml of distilled water and air-dried. The product obtained (2.45 g) is dissolved in 300 ml of dimethyl sulphoxide and, after addition of decolorizing charcoal, the solution is filtered. The filter is washed twice with 100 ml in total of dimethyl sulphoxide and the filtrate and washings are then combined, 400 ml of distilled water are added, they are stored for 30 minutes at 5° C. and then centrifuged. The supernatant solution is removed and the solid formed is then separated out by filtration, washed with 25 ml of distilled water and dried under reduced pressure (1 mmHg; 0.13 kPa) at 100° C. 1.3 g of 10-(4-oxo-5H,10H-imidazo[1,2-a]indeno [1,2-e]pyrazinylidene)-aminooxyacetic acid are thus obtained, decomposing without melting above 260° C. [N.M.R. spectrum: [300 MHz; (CD$_3$)$_2$SO d$_6$; δ in ppm]: mixture of isomers: 80% E isomer, 20% Z isomer: 5.05 and 5.08 (2s, 2H in total, =N—OCH$_2$—COO— of the E and Z isomer respectively); from 7.35 to 7.60 (mt, 2.2 H: —H7 and —H8 of the E and Z isomer and 1 of the —H of the imidazole for the Z isomer); 7.60 (s, 0.8H: 1 of the —H of the imidazole for the E isomer); 7.64 and 7.85–7.93 and 8.15 (4d, J=7.5 Hz, 0.2H and 0.8H respectively: —H6 and —H9 of the Z and E isomer respectively); 8.04 and 8.65 (2s, 1H in total: the other —H of the imidazole of the E and Z isomer respectively); 12.77 (cplx, 1H: —CO—NH—)].

EXAMPLE 37

To a suspension of 0.6 g of 10-amino-5H,10H-imidazo [1,2-a]indeno[1,2-e]pyrazin-4-one hydrochloride in 30 ml of anhydrous dimethylformamide, maintained under a nitrogen atmosphere at a temperature in the region of 0° C., are successively added 0.22 g of propionyl chloride and 0.4 g of triethylamine. The mixture is stirred for 3 hours 30 minutes and 0.22 g of propionyl chloride is added. The mixture is stirred for 1 hour at the same temperature and for 16 hours at a temperature in the region of 20° C. The insoluble material formed is removed by filtration and the filtrate is concentrated to dryness under reduced pressure (10 mmHg; 1.3 kPa) at 100° C. The product obtained (1.14 g) is dissolved at 40° C. in 10 ml of acetic acid and, after addition of 50 ml of distilled water, the solution is stirred for 1 hour at a temperature in the region of 20° C. The insoluble material formed is separated out by filtration, washed twice with 4 ml in total of distilled water and dried under reduced pressure (1 mmHg; 0.13 kPa) at 100° C. 0.26 g of 10-propionamido-5H,10H-imidazo[1,2-a]indeno-[1,2-e] pyrazin-4-one is thus obtained, decomposing without melting above 260° C. [N.M.R. spectrum: [200 MHz; (CD$_3$)$_2$SO d$_6$; δ in ppm]: 1.14 (t, J=7.5 Hz, 3H: —CH$_3$ ethyl); 2.28 (q, J=7.5 Hz, 2H: —COCH$_2$-ethyl); 6.18 (d, J=8.5 Hz, 1H: —CH— 10); 7.38 and 7.48 (2t broad, J=8 Hz, 1H each: —H7 and —H8); 7.52 and 7.88 (2d broad, J=8 Hz, 1H each: —H6 and —H9); 7.60 and 7.62 (2s, 1H each: —H of the imidazole); 8.48 (d, J=8.5 Hz, 1H: —NHCO— at 10); 12.43 (broad a, 1H: —CONH— of the ring)].

EXAMPLE 38

To a suspension of 1 g of 10-amino-5H,10H-imidazo[1,2-a]indeno[1,2-e]pyrazin-4-one hydrochloride in 50 ml of anhydrous dimethylformamide, maintained under an argon atmosphere at a temperature in the region of −10° C., are successively added 0.9 g of isobutyryl chloride and a solution of 0.4 g of triethylamine in 5 ml of anhydrous dimethylformamide. The mixture is stirred for 1 hour at the same temperature and 0.4 g of isobutyryl chloride is added. The mixture is stirred for 30 minutes at the same temperature and for 1 hour while allowing the temperature to return gradually to 20° C. The insoluble material formed is removed by filtration and the filtrate is concentrated to dryness under reduced pressure (15 mmHg; 2 kPa) at 70° C. The product obtained (1.63 g) is dissolved in 30 ml of methanol and, after addition of decolorizing charcoal, the solution is filtered, diluted with 40 ml of distilled water and stored for 45 minutes at a temperature in the region of 20° C. The insoluble material formed is separated out by filtration, washed with 5 ml of distilled water and with 5 ml of acetone and then dried under reduced pressure (1 mmHg; 0.13 kPa) at 100° C. 0.38 g of 10-isobutyramido-5H,10H-imidazo[1,2-a]indeno[1,2-e]-pyrazin-4-one is thus obtained, decomposing without melting above 260° C. [N.M.R. spectrum: [300 MHz; (CD$_3$)$_2$SO d$_6$; δ in ppm]: 1.09 and 1.12 [2d, J=7.5 Hz, 6H: —CH(CH$_3$)$_2$]; 2.48 [mt, 1H: —CH(CH$_3$)$_2$]; 6.15 (d, J=8.5 Hz, 1H: —CH— 10); 7.35 and 7.45 (2t broad, J=8.5 Hz, 1H each: —H7 and —H8); 7.47 and 7.85 (2d broad, J=8 Hz, 1H each: —H6 and —H9); 7.52 and 7.58 (2s, 1H each: —H of the imidazole); 8.46 (d, J=8.5 Hz, 1H: —NHCO— at 10); 12.48 (broad s, 1H: —CONH— of the ring)].

EXAMPLE 39

To a suspension of 0.6 g of 10-amino-5H,10H-imidazo [1,2-a]indeno[1,2-e]pyrazin-4-one hydrochloride in 30 ml of anhydrous dimethylformamide, maintained under a nitrogen atmosphere at a temperature in the region of −10° C., are successively added 0.29 g of benzenesulphonyl chloride and a solution of 0.4 g of triethylamine in 2 ml of anhydrous dimethylformamide and the mixture is stirred for 1 hour 30 minutes at the same temperature. 0.29 g of benzenesulphonyl chloride is added and the mixture is stirred for 2 hours 30 minutes, while allowing the temperature to rise gradually to 10° C. The insoluble material formed is removed by filtration and the filtrate is concentrated to dryness under reduced pressure (10 mmHg; 1.3 kPa) at 100° C. The product obtained (1.72 g) is dissolved in 6 ml of acetic acid at 40° C. and, after addition of 40 ml of distilled water, the solution is stirred for 1 hour. The insoluble material formed is separated out by filtration, washed twice with 4 ml in total of distilled water and dried under reduced pressure (1 mmHg; 0.13 kPa) at 100° C. 0.19 g of 10-benzenesulphonamido-5H,10H-imidazo[1,2-a]indeno-[1,2-e]pyrazin-4-one is thus obtained, melting at 216° C. [N.M.R. spectrum: [300 MHz; (CD$_3$)$_2$SO d$_6$; δ in ppm]: 5.71 (d, J=8.5 Hz, 1H: —CH— 10); 6.34 and 7.77 (2d broad, J=8 Hz, 1H each: —H6 and —H9); 7.08 and 7.36 (2t broad, J=8 Hz, 1H each: —H7 and —H8); 7.56 and 7.74 (2s, 1H each: —H of the imidazole); 7.68 (t, J=7.5 Hz, 2H: —H at 3 and —H at 5 of the phenylsulphonyl); 7.78 (t, J=7.5 Hz, 1H: —H at 4 of the phenylsulphonyl); 7.95 (d, J=7.5 Hz, 2H: —H at 2 and —H at 6 of the phenylsulphonyl); 8.62 (d, J=8.5 Hz, 1H: —NHCO— at 10); 12.46 (broad s, 1H: —CONH— of the ring)].

EXAMPLE 40

To a suspension of 0.92 g of 10-amino-5H,10H-imidazo [1,2-a]indeno[1,2-e]pyrazin-4-one hydrochloride in 20 ml of anhydrous dimethylformamide, maintained under a nitrogen atmosphere at a temperature in the region of 20° C., are added 1.1 g of triethylamine followed, dropwise over 10 minutes, by a solution of 1.25 g of phenyl isocyanate in 2 ml of anhydrous dimethylformamide and the mixture is stirred for 2 hours at the same temperature. The insoluble material formed is separated out by filtration, washed twice with 2 ml in total of dimethylformamide and dried under reduced pressure (5 mmHg; 0.65 kPa) at 100° C. The product obtained (0.9 g) is dissolved in 15 ml of dimethyl sulphoxide and, after addition of 15 ml of distilled water, the solution is stirred for 2 hours at a temperature in the region of 20° C. The insoluble material formed is separated out by filtration, washed twice with 2 ml in total of distilled water and dried under reduced pressure (1 mmHg; 0.13 kPa) at 100° C. 0.53 g of 10-(3-phenylureido)-5H,10H-imidazo[1,2-a]-indeno[1,2-e]pyrazin-4-one is thus obtained, decomposing without melting above 260° C. [N.M.R. spectrum: [200 MHz; (CD$_3$)$_2$SO d$_6$; δ in ppm]: 6.10 (d, J=8.5 Hz, 1H: —CH— 10); 6.91 (d, J=8.5 Hz, 1H: —NHCO— at 10); 7.00 (t, J=7.5 Hz, 1H: —H at 4 of the phenylcarbamoyl); 7.31 (t, J=7.5 Hz, 2H: —H at 3 and —H at 5 of the phenylcarbamoyl); 7.38 and 7.48 (2t broad, J=8 Hz, 1H each: —H7 and —H8); 7.52 (d, J=7.5 Hz, 2H: —H at 2 and —H at 6 of the phenylcarbamoyl); 7.60 and 7.85 (2s, 1H each: —H of the imidazole); 7.62 and 7.88 (2d broad, J=8 Hz, 1H each: —H6 and —H9); 8.68 (s, 1H: Ar—NO—CO); 12.50 (broad s, 1H: —CONH— of the ring)].

EXAMPLE 41

To a suspension of 0.92 g of 10-amino-5H,10H-imidazo[1,2-a]indeno[1,2-e]pyrazin-4-one hydrochloride in 20 ml of anhydrous dimethylformamide, maintained under a nitrogen atmosphere at a temperature in the region of 20° C., are added 1.1 g of triethylamine followed, dropwise over 5 minutes, by a solution of 0.6 g of methyl isocyanate in 2 ml of anhydrous dimethylformamide and the mixture is stirred for 2 hours at the same temperature. The insoluble material formed is separated out by filtration, washed twice with 2 ml in total of dimethylformamide, twice with 2 ml in total of acetone and dried under reduced pressure (5 mmHg; 0.65 kPa) at 100° C. The product obtained (0.35 g) is stirred in suspension for 5 minutes in 3 of boiling acetone and, after cooling and storing for 45 minutes at 5° C., the insoluble material is separated out by filtration, washed twice with 2 ml in total of methanol and dried under reduced pressure (1 mmHg; 0.13 kPa) at 100° C. 0.29 g of 10-(3-methylureido)-5H,10H-imidazo[1,2-a]indeno[2-e]-pyrazin-4-one is thus obtained, decomposing without melting above 260° C. [N.M.R. spectrum: [200 MHz; (CD$_3$)$_2$SO d$_6$; δ in ppm]: 2.70 (d, J=4.5 Hz, 3H: —CH$_3$); 6.02 (d, J=8.5 Hz, 1H: —CH— 10); 6.04 (d, J=4.5 Hz, 2H: —CONH—); 6.70 (d, J=8.5 Hz, 1H: —NHCO— at 10); 7.37 and 7.55 (2t broad, J=8 Hz, 1H each: —H7 and —H8); 7.53 and 7.85 (2d broad, J=8 Hz, 1H each: —H6 and —H9); 7.60 and 7.78 (2s, 1H each: —H of the imidazole); 12.46 (broad s, 1H: —CONH— of the ring)].

EXAMPLE 42

To a solution of 0.48 g of ammonium acetate in 120 ml of 28% aqueous ammonia solution are successively added 3.25 g of 8-fluoro-10-hydroxyimino-5H,10H-imidazo[1,2-a]indeno[1,2-e]pyrazin-4-one, 120 ml of ethanol and 3.55 g of zinc powder. The mixture is stirred for 2 hours at boiling and for 16 hours at a temperature in the region of 20° C., followed by dropwise addition of 60 ml of aqueous 5N hydrochloric acid solution and the mixture is stirred for 16 hours at the same temperature. The insoluble material formed is removed by filtration and the filtrate is concentrated to dryness under reduced pressure (10 mmHg; 1.3 kPa) at 50° C. The product obtained (13.4 g) is stirred in suspension in 30 ml of distilled water and the insoluble material is separated out by filtration, washed twice with 4 ml in total of distilled water and dried under reduced pressure (10 mmHg; 1.3 kPa) at 50° C. The product obtained (1.35 g) is suspended for 10 minutes in 10 ml of boiling methanol. After cooling and storing for 16 hours at 5° C., the insoluble material is separated out by filtration, washed with 1 ml of methanol and resuspended for 10 minutes in 5 ml of boiling methanol. After cooling and storing for 6 hours at 5° C., the insoluble material is separated out by filtration, washed with 1 ml of methanol and dried under reduced pressure (1 mmHg; 0.13 kPa) at 100° C. 0.48 g of 10-amino-8-fluoro-5H,10H-imidazo[1,2-a]-indeno[1,2-e]pyrazin-4-one hydrochloride is thus obtained, decomposing without melting above 260° C. [N.M.R. spectrum: |200 MHz; (CD$_3$)$_2$SO d$_6$; δ in ppm]: 5.69 (broad s, 1H: —CH— 10); 7.44 (dt, J=8.5 and 2 Hz, 1H: —H7); 7.68 and 8.54 (2s, 1H each: —H of the imidazole); 7.93 (dd, J=8.5 and 2 Hz, 1H: —H9); 7.94 (dd, J=8.5 and 6 Hz, 1H: —H6); 9.30 (cplx, 3H: —NH$_3^+$Cl$^-$; 12.72 (wide cplx, 1H: —CONH—)].

8-Fluoro-10-hydroxyimino-5H,10H-imidazo-[1,2-a]indeno[1,2-e]pyrazin-4-one may be prepared in the following way: 1.8 g of 80% sodium hydride are added over 15 minutes to a suspension, maintained at 20° C. and under an argon atmosphere, of 4.72 g of 8-fluoro-5H,10H-imidazo[1,2-a]indeno[1,2-e]pyrazin-4-one hydrochloride in 70 ml of anhydrous dimethyl sulphoxide. After stirring for 25 minutes, a solution of 2.3 g of isoamyl nitrite in 7 ml of anhydrous dimethyl sulphoxide is added dropwise over 20 minutes and the mixture is then stirred for 1 hour at the same temperature. 35 ml of distilled water are slowly added and the mixture is then poured into a mixture of 100 g of ice and 340 ml of distilled water, acidified with 4.1 ml of acetic acid and then centrifuged. After removal of the supernatant solution, the solid is suspended in 25 ml of acetone, filtered, washed twice with 20 ml in total of acetone and dried under reduced pressure (5 mmHg; 0.65 kPa) at 100° C. 4.45 g of 8-fluoro-10-hydroxyimino-5H,10H-imidazo[1,2-a]indeno-[1,2-e]pyrazin-4-one are thus obtained, as a mixture of the E and Z forms.

8-Fluoro-5H,10H-imidazo[1,2-a]indeno[1,2-e]-pyrazin-4-one [lacuna] may be obtained in the following way: 1.8 g of 1-[2-(5-fluoro-1-oxoindanyl)imidazole-2-carboxamide are dissolved in 90 ml of boiling methanol and, after addition of 0.1 g of decolorizing charcoal, the solution is filtered. The filter is washed with 20 ml of boiling methanol and the filtrate and washings are then combined, 27 ml of aqueous 12N hydrochloric acid solution are added and the mixture is stored for 3 hours at 5° C. The crystals are separated out by filtration, washed twice with 20 ml in total of chilled methanol and dried under reduced pressure (1 mmHg; 0.13 kPa) at 60° C. 1 g of 8-fluoro-5H,10H-imidazo[1,2-a]indeno[1,2-e]pyrazin-4-one hydrochloride is thus obtained, decomposing without melting above 300° C. [N.M.R. spectrum: (200 MHz; DMSO d$_6$; δ in ppm): 4.11 (s, 2H: —CH$_2$— at 10); 7.32 (ddd, J=9.5–8.5 and 2 Hz, 1H: —H7); 7.57 (dd, J=9.5 and 2 Hz, 1H: —H9); 7.97 (dd, J=8.5 and 5 Hz, 1H: —H6); 7.99 and 8.28 (2d, J=1.5 Hz, 1H each: —H of the imidazole); 13.13 (cplx, 1H: —CONH—)].

1-[2-(5-Fluoro-1-oxoindanyl)imidazole-2-carboxamide may be prepared in the following way: 2.2 g of ethyl 1-[2-(5-fluoro-1-oxoindanyl)]imidazole-2-carboxylate are dissolved in 80 ml of 2.5N ammoniacal methanol solution and the solution is stored for 20 hours at a temperature in the region of 20° C. and is then concentrated to dryness under reduced pressure (15 mmHg; 2 kPa) at 35° C. The product obtained is suspended in 50 ml of isopropyl ether, filtered, washed twice with 20 ml in total of isopropyl ether and then dried under reduced pressure (15 mmHg; 2 kPa) at a temperature in the region of 20° C. 1.85 g of 1-[2-(5-fluoro-1-oxoindanyl)imidazole-2-carboxamide are thus obtained, in the form of a solid melting at 221° C.

Ethyl 1-[2-(5-fluoro-1-oxoindanyl)]imidazole-2-carboxylate may be prepared in the following way: a solution of 13.3 g of ethyl imidazole-2-carboxylate in 145 ml of anhydrous dimethylformamide is added, dropwise over 20 minutes at a temperature between 20° C. and 25° C., to a suspension of 3.4 g of 80% sodium hydride in 45 ml of anhydrous dimethylformamide maintained under a nitrogen atmosphere. After stirring for 15 minutes, a solution of 26 g of 2-bromo-5-fluoro-1-indanone in 190 ml of anhydrous dimethylformamide is added dropwise over 10 minutes at the same temperature. The mixture is stirred for 1 hour 30 minutes and, after slow addition of 100 ml of water, is then poured into 3,800 ml of distilled water and extracted 4 times with 3,800 ml in total of chloroform. The organic extracts are combined, washed with 950 ml of distilled water, dried over anhydrous sodium sulphate and concentrated to dryness under reduced pressure (15 mmHg; 2 kPa) at 40° C. The product obtained (27 g) is chromatographed on 1,490 g of neutral silica gel (0.020–0.045 mm) contained in a column of diameter 9.6 cm, eluting under pressure with a dichloromethane/ethyl acetate mixture (70/30 by volume) and collecting 80 ml fractions. Fractions 13 to 70 are combined and concentrated to dryness under reduced pressure (15 mmHg; 2 kPa) at 40° C. 13.4 g of ethyl 1-[2-(5-fluoro-1-oxoindanyl)]-imidazole-2-carboxylate are thus obtained, melting at 127° C.

2-Bromo-5-fluoro-1-indanone may be prepared in the following way: a solution of 20.6 g of bromine in 90 ml of acetic acid is added, dropwise over 1 hour at 20° C., to a solution of 20 g of 5-fluoro-1-indanone and 0.1 ml of aqueous 47% hydrobromic acid in 260 ml of acetic acid. After stirring for 2 hours, the mixture is poured into 850 ml of distilled water and extracted 3 times with 850 ml in total of methylene chloride. The organic extracts are combined, washed with 200 ml of distilled water, dried over anhydrous sodium sulphate and concentrated to dryness under reduced pressure (15 mmHg; 2 kPa) at 30° C. The product obtained (31 g) is chromatographed on 1,860 g of neutral silica gel (0.020–0.045 mm) contained in a column of diameter 9.8 cm, eluting with a cyclohexane/ethyl acetate mixture (70/30 by volume) and collecting a fraction of 10.5 litres which is eliminated and then a fraction of 25 litres which is concentrated under reduced pressure (15 mmHg; 2 kPa) at 40° C. 28.4 g of 2-bromo-5-fluoro-1-indanone are thus obtained, in the form of a yellow oil [Rf=0.7; thin layer chromatography on silica gel; solvent: cyclohexane/ethyl acetate (70/30 by volume)].

EXAMPLE 43

To a suspension of 7 g of 10-formamido-5H,10H-imidazo[1,2-a]indeno[1,2-e]pyrazin-4-one in 225 ml of anhydrous tetrahydrofuran maintained at 0° C. are added, dropwise over 10 minutes, 62.5 ml of a 2M solution of borane/methyl sulphide complex in tetrahydrofuran. The mixture is stirred for 10 minutes at the same temperature and then for 18 hours at a temperature in the region of 20° C. After addition of 100 ml of methanol and stirring for 1 hour, the insoluble material is separated out by filtration and washed with 25 ml of methanol. The filtrate and the washings are combined and concentrated to dryness under reduced pressure (15 mmHg; 2 kPa) at 35° C. The product obtained (3.9 g) is chromatographed on 390 g of neutral silica gel (0.020–0.045 mm) contained in a column of diameter 5.3 cm, eluting with a chloroform/methanol/28% aqueous ammonia mixture (82/15/3 by volume) and collecting 35 ml fractions. Fractions 25 to 31 are combined and concentrated to dryness under reduced pressure (1 mmHg; 0.13 kPa) at 90° C. 0.59 g of 10-methylamino-5H,10H-imidazo[1,2-a]indeno[1,2-e]-pyrazin-4-one is thus obtained, melting at 184° C. [N.M.R. spectrum: [200 MHz; (CD$_3$)$_2$SO d$_6$; δ in ppm): 1.85 (s, 3H: —CH$_3$); 5.13 (s, 1H: —CH— 10); 7.36 and 7.43 (2t broad, J=8 Hz, 1H each: —H7 and —H8); 7.61 and 8.17 (2s broad, 1H each: —H of the imidazole); 7.62 and 7.85 (2d broad, J=8 Hz, 1H each: —H6 and —H9); 12.35 (broad s, 1H: —CONH— of the ring)].

10-Formamido-5H,10H-imidazo[1,2-a]indeno-[1,2-e]pyrazin-4-one may be prepared in the following way: a mixture of 21.4 g of acetic anhydride and 11.5 g of formic acid is heated for 2 hours at a temperature between 50° C. and 60° C. and cooled to 20° C. 0.9 g of anhydrous sodium acetate is then added followed, after dissolution, by 2.75 g of 10-amino-5H,10H-imidazo-[1,2-a]indeno[1,2-e]pyrazin-4-one hydrochloride. The mixture is stirred for 1 hour at 20° C. and is concentrated to dryness under reduced pressure (15 mmHg; 2 kPa) at 50° C. The product obtained (4.3 g) is dissolved in 50 ml of dimethylformamide and, after addition of decolorizing charcoal, the solution is filtered. 200 ml of distilled water are then added to the filtrate and the mixture is stored for 1 hour at a temperature in the region of 5° C. The insoluble material formed is separated out by filtration, washed with 10 ml of distilled water and dried under reduced pressure (1 mmHg; 0.13 kPa) at 100° C. 1.2 g of 10-formamido-5H,10H-imidazo[1,2-a]indeno[1,2-e]pyrazin-4-one are thus obtained, melting at 280° C. (decomposition) [N.M.R. spectrum: [200 MHz; (CD$_3$)$_2$SO d$_6$; δ in ppm): 6.22 (d, J=8.5 Hz, 1H: —CH— 10); 7.36 and 7.45 (2t broad, J=8 Hz, 2H: —H7 and —H8); 7.51 and 7.87 (2d broad, J=8 Hz, 2H: —H6 and —H9); 7.58 and 7.64 (2s, 1H each: —H of the imidazole); 8.44 (s, 1H: —CH=O); 8.78 (d, J=8.5 Hz, 1H: —CONH at 10); 12.50 (broad s, 1H: —CONH— of the ring)).

EXAMPLE 44

To a suspension of 1.05 g of 7-chloro-10-hydroxyimino-5H,10H-imidazo[1,2-a]indeno[1,2-e]-pyrazin-4-one in 35 ml of ethanol in the presence of 0.12 g of ammonium acetate and 35 ml of 28% aqueous ammonia are progressively added 1.07 g of zinc powder. The reaction mixture is brought to reflux for 5 hours. After cooling to a temperature in the region of 20° C., 45 ml of 6N hydrochloric acid are added dropwise to the reaction medium and stirring is continued for 24 hours at the same temperature. The precipitate formed is filtered off, washed with water and dried under reduced pressure (1 mmHg; 0.13 kPa) at 50° C. 0.35 g of 10-amino-7-chloro-5H,10H-imidazo[1,2-a]indeno[1,2-e]-pyrazin-4-one dihydrochloride trihydrate is thus obtained, in the form of a beige powder decomposing at 250° C. [N.M.R. spectrum: (250 MHz; DMSO d$_6$; δ in ppm): 5.70 (broad s, 1H: CH at 10); (dd, J=8 and 2 Hz, 1H: H-8); 7.67 and 8.57 (2d, J=1 Hz, 1H each: H of the imidazole); 8.01 (d, J=2 Hz, 1H: H-6); 8.01 (d, J=8 Hz, 1H: H-9); 9.30 (cplx, 1H: NH$_2$) 12.70 (cplx, 1H: CONH)].

7-Chloro-10-hydroxyimino-5H,10H-imidazo-[1,2-a]indeno[1,2-e]pyrazin-4-one may be obtained according to the following procedure: 0.97 g of 60% sodium hydride is added to a suspension of 2.5 g of 7-chloro-5H,10H-imidazo[1,2-a]indeno[1,2-e]pyrazin-4-one in 30 ml of anhydrous dimethyl sulphoxide. After stirring for 30 minutes at a temperature in the region of 20° C., a solution of 1.3 ml of isoamyl nitrite in 10 ml of dimethyl sulphoxide is added dropwise and the mixture is then stirred for 3 hours at the same temperature. 20 ml of distilled water are slowly added and the mixture is then poured into ice-water, acidified with acetic acid and then centrifuged. After removal of the supernatant solution, the solid is taken up in 20 ml of acetone and the insoluble material is filtered off, washed with methanol and dried. The product obtained (1.3 g) is suspended in 30 ml of dimethyl sulphoxide and the insoluble material is filtered off, washed with water and dried. The filtrate is treated with 100 ml of water and the precipitate formed is filtered off, washed with water and dried. The two insoluble materials thus isolated are combined, washed with water and dried under reduced pressure (1 mmHg; 0.13 kPa) at 50° C. 1.05 g of the expected product are obtained in the form of a green solid, the melting point of which is greater than 260° C.

7-Chloro-5H,10H-imidazo[1,2-a]indeno[1,2-e]-pyrazin-4-one may be obtained in the following way: 1 g of 1-[2-(6-chloro-1-oxoindanyl)]imidazole-2-carboxamide is dissolved in 50 ml of boiling methanol and, after addition of 0.1 g of decolorizing charcoal, the solution is filtered. The filter is washed with 25 ml of boiling methanol and the filtrate and washings are then combined, 15 ml of aqueous 12N hydrochloric acid solution are added and the mixture is stored for 3 hours at 5° C. The crystals are separated out by filtration, washed twice with 20 ml in total of chilled methanol and dried under reduced pressure (1 mmHg; 0.13 kPa) at 60° C. 0.4 g of 7-chloro-5H,10H-imidazo-[1,2-a]indeno[1,2-e]pyrazin-4-one hydrochloride is thus obtained, decomposing without melting above 300° C. [N.M.R. spectrum: (300 MHz; DMSO $d_6$; δ in ppm): 4.12 (s, 2H: —$CH_2$— at 10); 7.44 (dd, J=8 and 1 Hz, 1H: —H8); 7.66 (dd, J=8 Hz, 1H: —H9); 7.95 and 8.25 (2s broad, 1H each: —H of the imidazole); 8.05 (d, J=1 Hz, 1H: —H6); 12.97 (cplx, 1H: —CONH—)].

1-[2-(6-Chloro-1-oxoindanyl)]imidazole-2-carboxamide may be prepared in the following way: 1.2 g of ethyl 1-[2-(6-chloro-1-oxoindanyl)]imidazole- 2-carboxylate are dissolved in 45 ml of 2.5N ammoniacal methanol solution and the solution is stored for 20 hours at a temperature in the region of 20° C. and is then concentrated to dryness under reduced pressure (15 mmHg; 2 kPa) at 35° C. The product obtained is suspended in 50 ml of isopropyl ether, filtered, washed twice with 20 ml in total of isopropyl ether and then dried under reduced pressure (15 mmHg; 2 kPa) at a temperature in the region of 20° C. 1 g of 1-[2-(6-chloro-1-oxoindanyl)]imidazole-2-carboxamide is thus obtained, in the form of a solid melting at 190° C.

Ethyl 1-[2-(6-chloro-1-oxoindanyl)]imidazole-2-carboxylate may be prepared in the following way: a solution of 2.5 g of ethyl imidazole-2-carboxylate in 30 ml of anhydrous dimethylformamide is added, dropwise over 20 minutes at a temperature between 20° C. and 25° C., to a suspension of 0.7 g of 80% sodium hydride in 30 ml of anhydrous dimethylformamide maintained under a nitrogen atmosphere. After stirring for 15 minutes, a solution of 5.4 g of 2-bromo-6-chloro-1-indanone in 10 ml of anhydrous dimethylformamide is added dropwise over 10 minutes at the same temperature. The mixture is stirred for 1 hour 30 minutes and, after slow addition of 100 ml of water, is then poured into 3,800 ml of distilled water and extracted 4 times with 3,800 ml in total of chloroform. The organic extracts are combined, washed with 950 ml of distilled water, dried over anhydrous sodium sulphate and concentrated to dryness under reduced pressure (15 mmHg; 2 kPa) at 40° C. After chromatography on silica gel using a dichloromethane/ethyl acetate mixture (70/30 by volume), 1 g of ethyl 1-[2-(6-chloro-1-oxoindanyl)]-imidazole-2-carboxylate is obtained, melting at 180° C.

2-Bromo-6-chloro-1-indanone may be prepared as described in German Patent 2,640,358.

EXAMPLE 45

To 0.5 g of 10-amino-7-chloro-5H,10H-imidazo-[1,2-a]indeno[1,2-e]pyrazin-4-one hydrochloride suspended in 8 ml of dimethyl sulphoxide is added dropwise 0.45 ml of triethylamine, followed by a solution of 0.9 ml of phenyl isocyanate in 2 ml of dimethylformamide. The reaction medium is stirred for 2 hours at a temperature in the region of 20° C. and the precipitate formed is filtered off, washed with water and dried under reduced pressure (1 mmHg; 0.13 kPa) at 50° C. 0.15 g of 7-chloro-10-(3-phenylureido)-5H,10H-imidazo[1,2-a]indeno[1,2-e]pyrazin-4-one is thus obtained, in the form of a white solid the melting point of which is greater than 260° C. (Analysis $C_{20}H_{14}ClN_5O_2 \cdot 0.6$ DMF·0.8 $H_2O$ % calculated C: 61.31; H: 3.60; Cl: 9.05; N: 17.87; % found C: 61.1; H: 3.5; Cl: 9.4; N: 17.7).

EXAMPLE 46

To 0.8 g of 7-chloro-10-formamido-5H,10H-imidazo[1,2-a]indeno[1,2-e]pyrazin-4-one suspended in 25 ml of anhydrous dioxane at 10° C. are added 6.7 ml of 2M borane/dimethyl sulphide solution in tetrahydrofuran over approximately 1 hour. The reaction mixture is stirred for 15 hours at a temperature in the region of 20° C. and is then treated with 20 ml of methanol and left for an additional 1 hour at the same temperature. After concentration to dryness under reduced pressure (15 mmHg; 2 kPa), the residue obtained is purified by flash chromatography on a column of silica, using a mixture of dichloromethane and methanol (95/5 by volume) as eluent. The product obtained (0.43 g) dissolved in a mixture of ethanol and methanol (1/1 by volume) is acidified using hydrochloric ether to give 0.24 g of 7-chloro-10-methylamino-5H,10H-imidazo-[1,2-a]indeno[1,2-e]pyrazin-4-one hydrochloride, in the form of a greenish-white powder the melting point of which is greater than 260° C. (Analysis $C_{20}H_{14}ClN_5O_2 \cdot 0.24$ EtOH·0.15 $H_2O$ % calculated C: 44.53; H: 4.00; Cl: 28.16; N: 14.84; % found C: 44.5; H: 3.9; Cl: 28.1; N: 14.7).

7-Chloro-10-formamido-5H,10H-imidazo[1,2-a]-indeno[1,2-e]pyrazin-4-one may be obtained in the following way: 4 ml of formic acid are added slowly to 8 ml of acetic anhydride and the mixture is heated to 50° C. for 2 hours. After cooling to a temperature in the region of 20° C., 0.4 g of sodium acetate is added to the mixture, followed portionwise by 1.25 g of 10-amino-7-chloro-5H,10H-imidazo[1,2-a]indeno[1,2-e]pyrazin-4-one hydrochloride. The suspension is stirred for 1 hour at the same temperature. The precipitate is filtered off, washed with water and dried under reduced pressure (1 mmHg; 0.13 kPa) at 50° C. to give 0.88 g of the expected product in the form of a bluish solid, the melting point of which is greater than 260° C.

EXAMPLE 47

2.1 g of 10-benzylidene-7-chloro-5H,10H-imidazo[1,2-a]indeno[1,2-e]pyrazin-4-one dissolved in 20 ml of a mixture of methanol and dimethylformamide (1/1 by volume) are hydrogenated at a temperature in the region of 20° C. and at a pressure of 9.6 bar of hydrogen for 24 hours in the presence of 10% palladium on charcoal. The catalyst is then filtered off under inert atmosphere and the solvents are evaporated off. The brown oil obtained is taken up in 25 ml of methanol and, after addition of 50 ml of distilled water, a pink precipitate forms. The solid thus obtained (1.3 g) is recrystallized in 150 ml of a mixture of methanol and water (1/2 by volume). 0.6 g of 10-benzyl-7-chloro-5H,10H-imidazo[1,2-a]indeno[1,2-e]pyrazin-4-one is obtained, in the form of a beige solid the melting point of which is greater than 260° C. (Analysis $C_{20}H_{14}ClN_3O \cdot 0.41$ $H_2O$ % calculated C: 69.07; H: 4.06; Cl: 10.19; N: 12.08; % found C: 69.0; H: 3.9; Cl: 10.5; N: 12.4).

10-Benzylidene-7-chloro-5H,10H-imidazo-[1,2-a]indeno[1,2-e]pyrazin-4-one may be prepared in the following way:

to a mixture of 2 g of 7-chloro- 5H,10H-imidazo[1,2-a]indeno[1,2-e]pyrazin-4-one and 1.2 ml of benzaldehyde in 60 ml of dimethyl sulphoxide is progressively added 0.78 g of 60% sodium hydride. The reaction is continued for 5 hours at a temperature in the region of 20° C. After cooling to 10° C., 5 ml of acetic acid are added dropwise, followed by 200 ml of distilled water. The precipitate formed is filtered off, washed with water and dried to give 2.4 g of the expected product in the form of a brown solid, the melting point of which is greater than 260° C.

EXAMPLE 48

To a stirred mixture, at a temperature in the region of 20° C. and under cover of argon, of 0.48 g of 10-methyl-5H, 10H-imidazo[1,2-a]indeno[1,2-e]pyrazin-4-one and 25 ml of dimethylformamide is added 0.21 g of 80% sodium hydride and the stirring is continued for 15 minutes. 0.12 g of 80% sodium hydride is then added followed, after stirring for 15 minutes, by 0.28 ml of trimethylchlorosilane. The stirring is continued for 15 minutes and 0.24 ml of 4-vinylpyridine are then added and the stirring is continued for 90 minutes. The reaction mixture is treated with 20 g of ice and 0.7 ml of acetic acid and filtered, and the filtrate is concentrated on a rotary evaporator. The evaporation residue is triturated with 40 ml of 2-propanol and filtered, and the filtrate is again concentrated to give a red oil. This oil is acidified with 5 ml of 1N hydrochloric acid, washed with dichloromethane (2×25 ml) and basified with sodium hydrogen carbonate solution. Two extractions with dichloromethane (2×25 ml) are carried out on this alkaline phase and the organic extract is concentrated on a rotary evaporator. The evaporation residue is purified by chromatography on silica gel (60 g), eluting with a mixture of dichloroemthane/methanol (95/5 by volume) to give a colourless lacquer. This lacquer is triturated with 5 ml of ethyl acetate and then with 2×10 ml of isopropyl ether and 25 ml of petroleum ether (40°–65° C.) and gives, after drying at 60° C. under vacuum (1 mmHg; 0.13 kPa), 0.21 g of 10-methyl-10-[2-(4-pyridyl)ethyl]-5H,10H-imidazo[1,2-a]indeno[1,2-e]pyrazin-4-one, in the form of an off-white solid melting at about 200° C. (Analysis % calculated C: 73.67, H: 5.30, N: 16.36, O: 4.67, % found C: 73.8, H: 5.7, N: 16.3).

The medicaments according to the invention consist of a compound of formula (I) or a salt of such a compound, in the pure state or in the form of a composition in which it is combined with any other pharmaceutically compatible product, which may be inert or physiologically active. The medicaments according to the invention may be employed via the oral, parenteral, rectal or topical route.

As solid compositions for oral administration, tablets, pills, powders (gelatin capsules or wafer capsules) or granules may be used. In these compositions, the active principle according to the invention is mixed with one or more inert diluents, such as starch, cellulose, sucrose, lactose or silica, under a stream of argon. These compositions may also contain substances other than diluents, for example one or more lubricating agents such as magnesium stearate or talc, a dye, a coating agent (dragees) or a varnish.

As liquid compositions for oral administration, pharmaceutically acceptable solutions, suspensions, emulsions, syrups and elixirs containing inert diluents such as water, ethanol, glycerol, vegetable oils or paraffin oil may be used. These compositions may contain substances other than diluents, for example wetting, sweetening, thickening, flavouring or stabilizing products.

The sterile compositions for parenteral administration may preferably be aqueous or non-aqueous solutions, suspensions or emulsions. Water, propylene glycol, a polyethylene glycol, vegetable oils, in particular olive oil, injectable organic esters, for example ethyl oleate, or other suitable organic solvents may be employed as solvent or vehicle. These compositions may also contain adjuvants, in particular wetting, tonicity, emulsifying, dispersing and stabilizing agents. The sterilization may be effected in several ways, for example by aseptic filtration, by incorporating sterilizing agents into the composition, by irradiation or by heating. They may also be prepared in the form of sterile solid compositions which may be dissolved at the time of use in sterile water or any other injectable sterile medium.

The compositions for rectal administration are suppositories or rectal capsules which contain, besides the active product, excipients such as cocoa butter, semi-synthetic glycerides or polyethylene glycols.

The compositions for topical administration may for example be creams, lotions, eyedrops, mouthwashes, nasal drops or aerosols.

In human therapy, the compounds according to the invention are particularly useful for the treatment and/or prevention of the conditions which require the administration of an antagonist of the AMPA receptor or of an antagonist of the NMDA receptor. These compounds are in particular useful for treating or preventing all ischemias and in particular cerebral ischemia, the effects of anoxia, the development of neurodegenerative diseases, Huntington's chorea, Alzheimer's disease, amyotrophic lateral sclerosis, olivopontocerebellar atrophy and Parkinson's disease, with regard to epileptogenic and/or convulsive symptoms, for the treatment of cerebral or spinal trauma, trauma associated with degeneration of the inner ear or of the retina, of anxiety, depression, schizophrenia, Tourette's syndrome, hepatic encephalopathy, as analgesics, as anti-inflammatory agents, as anti-anorexic agents, as anti-migraine and anti-emetic agents and for the treatment of poisoning by neurotoxins or other substances which are agonists of the NMDA receptor, as well as neurological problems associated with viral diseases such as AIDS, rabies, measles and tetanus. These compounds are also useful for the prevention of the withdrawal symptoms to drugs and alcohol, and for inhibiting the addiction to and dependency on opiates, and for the treatment of deficiencies associated with mitochondrial anomalies such as mitochondrial myopathy, Leber's syndrome, Wernicke's encephalopathy, Rett's syndrome, homocysteinaemia, hyperprolinaemia, hydroxybutyric aminoaciduria, Lead's encephalopathy and sulphite oxidase deficiency.

The doses depend upon the effect sought, the duration of the treatment and the administration route used; they are generally between 10 mg and 100 mg per day via the oral route for an adult with unit doses ranging from 5 mg to 50 mg of active substance.

Generally speaking, the doctor will determine the appropriate dosage depending on the age, weight and all the other factors which are specific to the subject to be treated.

The examples which follow illustrate compositions according to the invention:

EXAMPLE A

Gelatin capsules containing 50 mg of active product and having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

Tablets containing 50 mg of active product and having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethyl cellulose, glycerine and titanium oxide (72/3.5/24.5) q.s. 1 finished film-coated tablet weighing 245 mg | |

EXAMPLE C

An injectable solution containing 10 mg of active product and having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| 95% Ethanol | 0.4 ml |
| Sodium hydroxide | 24 mg |
| Propylene glycol | 1.6 ml |
| Water q.s. | 4 ml |

We claim:
1. A compound of formula (I) or a salt thereof:

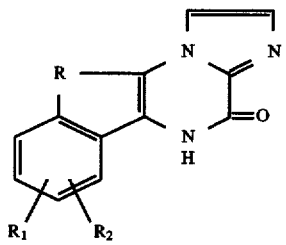

(I)

in which when R represents a C=$R_3$, C($R_4$)$R_5$ or CH—$R_6$ radical, $R_1$ and $R_2$, which may be identical or different, each represent hydrogen, a halogen atom or an alkyl, alkoxy, amino, acylamino, —NH—CO—NH—Ar, —N=CH—N(alk)alk', nitro, cyano, phenyl, imidazolyl or $SO_3H$ radical, $R_3$ represents an oxygen atom or an NOH, NO-alk-COOX or CH—$R_7$ radical, $R_4$ represents an alkyl, -alk-Het or -alk-Ar radical, $R_5$ represents an alkyl containing from 1 to 11 carbon atoms and being either a straight or branched chain, an -alk-Het or an -alk-Ar radical, or $R_4$ and $R_5$ may together, with the carbon atom to which they are attached, form a cycloalkyl radical, $R_6$ represents a hydroxyl, an alkyl containing from 1 to 11 carbon atoms and being either a straight or branched chain, an $NR_8R_9$, an -alk-OH, an -alk-$NR_8R_9$, an -alk-Ar or an -alk-Het radical, $R_7$ represents a hydroxyl, alkyl, phenyl, -alk-Ar, -alk-Het or $NR_{10}R_{11}$ radical, or a pyridyl, furyl, quinolyl, pyrazinyl or piperidyl radical, $R_8$ and $R_9$, which may be identical or different, each represent an alkyl radical, or $R_8$ represents a hydrogen atom, and $R_9$ represents a hydrogen atom or an alkyl, —$COR_{12}$, —$CSR_{30}$ or —$SO_2R_{13}$ radical, $R_{10}$ and $R_{11}$, which may be identical or different, each represent an alkyl or cycloalkyl radical, $R_{12}$ represents an alkyl, cycloalkyl, phenyl, —COO-alk, —$CH_2$—COOX, —$CH_2$—$NH_2$, —NH-alk, —$NH_2$, —NH—Ar or —NH-Het radical, $R_{13}$ represents an alkyl or phenyl radical, $R_{30}$ represents an —NH-alk, —NH—Ar, —$NH_2$ or —NH-Het radical, alk represents an alkyl or alkylene radical, alk' represents an alkyl radical, X represents a hydrogen atom or an alkyl radical, Ar represents a phenyl radical, and Het represents a pyridyl, furyl, quinolyl, pyrazinyl or piperidyl ring system, or when R represents a CH—$R_6$ radial, $R_6$ represents a 2-imidazolylmethyl radical and $R_1$ and $R_2$ each represent a hydrogen atom, wherein said alkyl and alkylene radicals and said alkyl and alkylene portions contain from 1 to 4 carbon atoms in a straight or branched chain, said acyl portions contain from 2 to 4 carbon atoms, and said cycloalkyl radicals contain from 3 to 6 carbon atoms; and including isomers of the compounds of formula (I) wherein $R_3$ represents an NOH, NO-alk-COOX or CH—$R_7$ radical, and racemic mixtures and enantiomers of the compounds of formula (I) wherein R represents a C($R_4$)$R_5$ radical in which $R_4$ is different from $R_5$ or CH—$R_6$.

2. A compound of formula (I) according to claim 1, wherein when R represents a C=$R_3$, C($R_4$)$R_5$ or CH—$R_6$ radical, $R_1$ and $R_2$ each represent a hydrogen or halogen atom, $R_3$ represents an oxygen atom or an NO-alk-COOX or CH—$R_7$ radical, $R_4$ represents an alkyl or an -alk-Ar radical, $R_5$ represents an alkyl which may contain from 1 to 11 carbon atoms and which may have a straight or branched chain, an -alk-Het or an -alk-Ar radical, or $R_4$ and $R_5$ may together, with the carbon atom to which they are attached, form a cycloalkyl radical, $R_6$ represents a hydroxyl, an alkyl containing from 1 to 11 carbon atoms and being either a straight or branched chain, an —$NR_8R_9$, an -alk-$NR_8R_9$, an -alk-OH, an -alk-Ar or an -alk-Het radical, $R_7$ represents a hydroxyl, a —$NR_{10}R_{11}$, radical or a pyridyl, furyl, quinolyl, pyrazinyl or piperidyl radical, $R_8$ represents a hydrogen atom, and $R_9$ represents a hydrogen atom or an alkyl, —$COR_{12}$ or —$SO_2R_{13}$ radical, $R_{10}$ and $R_{11}$, which may be identical or different, each represent an alkyl radical, $R_{12}$ represents an alkyl, —NH—Ar, —NH-alk or phenyl radical, $R_{13}$ represents an alkyl or phenyl radical, alk represents an alkyl or alkylene radical, X represents an alkyl radical, and Het represents a pyridyl, furyl, quinolyl, pyrazinyl or piperidyl radical, and when R represents a CH—$R_6$ radical, $R_6$ represents a 2-imidazolylmethyl radical. $R_1$ and $R_2$ are each hydrogen atoms; and including isomers of the compounds of formula (I) wherein $R_3$ represents an NO-alk-COOX or CH—$R_7$ radical, the racemic mixtures and the enantiomers of the compounds of formula (I) wherein R represents a $C(R_4)R_5$ radical in which $R_4$ is different from $R_5$ or CH—$R_6$.

3. A compound of formula (I) according to claim 1, selected from the compounds:

10-hydroxy-5H,10H-imidazo[1,2-a]indeno[1,2-e] pyrazin-4-one, 10-acetamido-5H,10H-imidazo[1,2-a]indeno[1,2-e] pyrazin-4-one, 10-amino-5H,10H-imidazo[1,2-a]indeno[1,2-e]pyrazin-4-one, 10-(E-dimethylaminomethylene)-5H,10H-imidazo-[1,2-a]indeno [1,2-e]pyrazin-4-one, 10-hydroxymethylene-5H,10H-imidazo[1,2-a]indeno-[1,2-e]pyrazin-4-one, 10,10-dimethyl-5H,10H-imidazo[1,2-a]indeno[1,2-e] pyrazin-4-one, spiro[5H,10H-imidazo[1,2-a]indeno[1,2-e]pyrazine-10:1'-cyclopropane]-4-one, spiro[5H,10H-imidazo[1,2-a]indeno[1,2-e]pyrazine-10:1'-cyclopentane]-4-one, 10-methyl-5H,10H-imidazo[1,2-a]indeno[1,2-e]pyrazin-4-one, 10,10-dibenzyl-5H,10H-imidazo[1,2-a]indeno[1,2-e] pyrazin-4-one, 10-hydroxymethyl-5H,10H-imidazo[1,2-a]indeno[1,2-e] pyrazin-4-one, 10-(2-furylmethyl)-5H,10H-imidazo[1,2-a]indeno[1,2-e] pyrazin-4-one, 10-(4-pyridylmethylene)-5H,10H-imidazo[1,2-a]indeno [1,2-e]-pyrazin-4-one, 10-(4-pyridylmethyl)-5H,10H-imidazo[1,2-a]indeno[1,2-e]-pyrazin-4-one, 10-(phenylpropyl)-5H,10H-imidazo[1,2-a]indeno[1,2-e] pyrazin-4-one, 10-(3-pyridylmethylene)-5H,10H-imidazo[1,2-a]indeno [1,2-e]-pyrazin-4-one, 10-(3-pyridylmethyl)-5H,10H-imidazo[1,2-a]indeno[1,2-e]-pyrazin-4-one, 10-(2-pyridylmethyl)-5H,10H-imidazo[1,2-a]indeno[1,2-e]-pyrazin-4-one, 10-(2-imidazolylmethyl)-5H,10H-imidazo[1,2-a]indeno [1,2-e]-pyrazin-4-one, tert-butyl (4-oxo-5H,10H-imidazo[1,2-a]indeno[1,2-e] pyrazine-10-ylidene)aminooxyacetate, 10-isobutyl-5H,10H-imidazo[1,2-a]indeno[1,2-e] pyrazin-4-one, (4-oxo-5H,10H-imidazo[1,2-a]indeno[1,2-e]pyrazine-10-ylidene)aminooxyacetic acid, 10-propionamido-5H,10H-imidazo[1,2-a]indeno[1,2-e] pyrazin-4-one, 10-amino-8-fluoro-5H,10H-imidazo[1,2-a]indeno[1,2-e] pyrazin-4-one, 10-(4-quinolylmethylene)-5H,10H-imidazo[1,2-a]indeno [1,2-e]-pyrazin-4-one, 10-(4-quinolylmethyl)-5H,10H-imidazo[1,2-a]indeno[1,2-e]-pyrazin-4-one, 10-(3-phenylureido)-5H,10H-imidazo[1,2-a]indeno[1,2-e]-pyrazin-4-one, 10-(3-methylureido)-5H,10H-imidazo[1,2-a]indeno[1,2-e]-pyrazin-4-one, 10-isobutyramido-5H,10H-imidazo[1,2-a]indeno[1,2-e] pyrazin-4-one, 10-amino-7-chloro-5H,10H-imidazo[1,2-a]indeno[1,2-e] pyrazin-4-one, 10-benzenesulphonylamido-5H,10H-imidazo[1,2-a] indeno[1,2-e]-pyrazin-4-one, 10-methylamino-5H,10H-imidazo[1,2-a]indeno[1,2-e] pyrazin-4-one, 10-(2-pyrazinylmethylene)-5H,10H-imidazo[1,2-a] indeno[1,2-e]-pyrazin-4-one, 10-(2-pyrazinylmethyl)-5H,10H-imidazo[1,2-a]indeno[1,2-e]-pyrazin-4-one, 10-benzyl-7-chloro-5H,10H-imidazo[1,2-a]indeno[1,2-e] pyrazin-4-one, 7-chloro-10-(3-phenylureido)-5H,10H-imidazo[1,2-a] indeno-[1,2-e]pyrazin-4-one, 10-(2-hydroxyethyl)-5H,10H-imidazo[1,2-a]indeno[1,2-e]-pyrazin-4-one, 7-chloro-10-methylamino-5H,10H-imidazo[1,2-a]indeno [1,2-e]-pyrazin-4-one, 10-benzyl-10-methyl-5H,10H-imidazo[1,2-a]indeno[1,2-e]-pyrazin-4-one, 10-methyl-10-(4-pyridylmethyl)-5H,10H-imidazo[1,2-a] indeno-[1,2-e]pyrazin-4-one, 10-(4-piperidylmethyl)-5H,10H-imidazo[1,2-a]indeno [1,2-e]-pyrazin-4-one, 5H,10H-imidazo[1,2-a]indeno[1,2-e]pyrazine-4,10-dione, 10-benzyl-5H,10H-imidazo[1,2-a]indeno[1,2-e]pyrazin-4-one, 10-hexyl-5H,10H-imidazo[1,2-a]indeno[1,2-e]pyrazin-4-one, 10-benzamido-5H,10H-imidazo[1,2-a]indeno[1,2-e] pyrazin-4-one, and 10-methyl-10-[2-(4-pyridyl)ethyl]-5H,10H-imidazo[1,2-a]-indeno[1,2-e]pyrazin-4-one and their salts.

4. A process for the preparation of a compound of formula (I) according to claim 1, wherein R represents a C=$R_3$ radical in which $R_3$ represents an oxygen atom, comprising the steps of hydrolyzing a compound of formula (I) wherein R represents a C=$R_3$ radical and $R_3$ represents a NOH radical, isolating said hydrolyzed product, and optionally converting said isolated product to a salt.

5. A pharmaceutical composition, which comprises an effective amount of at least one compound of formula (I) according to claim 1 and a pharmaceutically compatible carrier.

6. A pharmaceutical composition for antagonizing a AMPA receptor, which comprises an effective amount of at least one compound of formula (I) according to claim 1 and a pharmaceutically compatible carrier.

7. A pharmaceutical composition for antagonizing a NMDA receptor, which comprises an effective amount of at least one compound of formula (I) according to claim 1 and a pharmaceutically compatible carrier.

* * * * *

UNITED STATES PATENT AND TRADEMARK OFFICE
CERTIFICATE OF CORRECTION

PATENT NO. : 5,753,657
DATED : May 19, 1998
INVENTOR(S) : Jean-Claude ALOUP et al.

It is certified that error appears in the above-identified patent and that said Letters Patent is hereby corrected as shown below:

Title Page, item [57], line 7, (line 5 below formula (I)), "No-alk-COOK" should read --NO-alk-COOX--.

Claim 1, column 46, line 33, "radial" should read --radical--.

Claim 3, column 48, line 33, "10--" should read --10- --.

Signed and Sealed this

Seventh Day of March, 2000

Attest:

Q. TODD DICKINSON

*Attesting Officer*     *Commissioner of Patents and Trademarks*